US011254956B2

(12) United States Patent
Díez García et al.

(10) Patent No.: US 11,254,956 B2
(45) Date of Patent: Feb. 22, 2022

(54) *MYCELIOPHTHORA THERMOPHILA* HOST CELL HAVING IMPROVED CELLULOLYTIC ACTIVITY AND ENZYMATIC COMPOUNDS PRODUCED WITH SAME

(71) Applicant: ABENGOA BIOENERGÍA NUEVAS TECNOLOGÍAS, S.A., Seville (ES)

(72) Inventors: Bruno Díez García, Seville (ES); Noelia Valbuena Crespo, Seville (ES); Francisco Reyes Sosa, Seville (ES); Antonio Javier Moreno Pérez, Seville (ES); Dolores Pérez Gómez, Seville (ES); Ana Isabel Platero Gómez, Seville (ES); Lucía Martín Pérez, Seville (ES); Sandra Gavaldá Martín, Seville (ES); Laura Viñas De La Cruz, Seville (ES); Laura Sánchez Zamorano, Seville (ES); Consolación Álvarez Núñez, Seville (ES); María De Los Ángeles Bermúdez Alcántara, Seville (ES); Javier Rocha Martín, Seville (ES); Laura Ledesma García, Seville (ES); Ricardo Arjona Antolín, Seville (ES); Juan Luis Ramos Martín, Seville (ES)

(73) Assignee: ABENGOA BIOENERGÍA NUEVAS TECNOLOGÍAS, S.A., Seville (ES)

( * ) Notice: Subject to any disclaimer, the term of this patent is extended or adjusted under 35 U.S.C. 154(b) by 0 days.

(21) Appl. No.: 16/303,088

(22) PCT Filed: May 22, 2017

(86) PCT No.: PCT/ES2017/070339
§ 371 (c)(1),
(2) Date: Jun. 11, 2019

(87) PCT Pub. No.: WO2017/198890
PCT Pub. Date: Nov. 23, 2017

(65) Prior Publication Data
US 2019/0300914 A1    Oct. 3, 2019

(30) Foreign Application Priority Data
May 20, 2016   (ES) .............................. ES201630658

(51) Int. Cl.
| *C12P 7/06* | (2006.01) |
| *C12P 7/02* | (2006.01) |
| *C12N 9/14* | (2006.01) |
| *C12N 9/24* | (2006.01) |
| *C12P 7/10* | (2006.01) |
| *C12P 19/14* | (2006.01) |
| *C12N 1/14* | (2006.01) |
| *C12R 1/645* | (2006.01) |

(52) U.S. Cl.
CPC ............... *C12P 7/10* (2013.01); *C12N 1/145* (2021.05); *C12P 19/14* (2013.01); *C12R 2001/645* (2021.05); *Y02E 50/10* (2013.01)

(58) Field of Classification Search
CPC .... C12P 19/14; C12P 7/06; C12P 7/10; C12P 19/04; C12P 7/04; C12N 9/2437; C12N 9/58; C12N 9/2445; C12Y 302/01004; C12Y 302/01021; C12Y 302/01176
USPC ...... 435/252.3, 254.11, 320.1, 200, 209, 189
See application file for complete search history.

(56) References Cited

U.S. PATENT DOCUMENTS

| 7,399,627 B2 | 7/2008 | Emalfarb et al. |
| 2008/0194005 A1 | 8/2008 | Emalfarb et al. |

FOREIGN PATENT DOCUMENTS

| WO | WO0020555 A2 | 4/2000 |
| WO | WO 2009018537 A2 | 2/2009 |
| WO | WO 2010107303 A2 | 9/2010 |

OTHER PUBLICATIONS

Visser, H. et al. "Development of a mature fungal technology and production platform for industrial enzymes based on a *Myceliophthora thermophila* isolate, previously known as *Chrysosporium lucknowense* C1". Industrial Biotechnology, Jun. 1, 2011, vol. 7, No. 3, pp. 214-223.

Langston et al. , "Oxidoreductive Cellulose Depolymerization by the Enzymes Cellobiose Dehydrogenase and Glycoside Hydrolase 61", Applied And Environmental Microbiology, vol. 77, No. 19, Oct. 2011, pp. 7007-7015.

Mosier et al., "Features of promising technologies for pretreatment of lignocellulosic biomass", Bioresource Technology 96, Issue 6, Apr. 2005, pp. 673-686.

Nguyen et al., "Dilute Acid Pretreatment of Softwoods", Applied Biochemistry and Biotechnology, Mar. 1998, vol. 70, Issue 1, pp. 77-87.

Verdoes et al., "A dedicated vector for efficient library construction and high throughput screening in the hyphal fungus Chrysosporium lucknowense", Industrial Biotechnology, vol. 3, No. 1, Apr. 5, 2007.

(Continued)

*Primary Examiner* — Robert B Mondesi
*Assistant Examiner* — Mohammad Y Meah
(74) *Attorney, Agent, or Firm* — Womble Bond Dickinson (US) LLP

(57) ABSTRACT

The invention relates to a host cell, preferably a *Myceliophthora thermophila* cell, which presents a lower expression and/or secretion of non-contributory cellulolytic enzymes, preferably where the non-contributory cellulolytic enzyme is endoglucanase 6 comprising SEQ ID NO: 2, thereby promoting the presence of contributory cellulolytic enzymes in the enzymatic cocktail synthesised by said host cell. The invention also relates to the use of said host cells and the enzymatic cocktails synthesised by said host cells for the production of fermentable sugars of biomass and a method for producing bioproducts, preferably bioethanol, comprising the use of said host cell or the composition according to the invention.

6 Claims, 5 Drawing Sheets

Specification includes a Sequence Listing.

(56) References Cited

OTHER PUBLICATIONS

Jonathan Woodward, "Synergism in Cellulase Systems", Bioresource Technology, vol. 36, Issue 1, 1991, pp. 67-75.
International Search Report & Written Opinion of the International Searching Authority dated Aug. 25, 2017, for PCT application No. PCT/ES2017/070339.

MYCELIOPHTHORA THERMOPHILA HOST CELL HAVING IMPROVED CELLULOLYTIC ACTIVITY AND ENZYMATIC COMPOUNDS PRODUCED WITH SAME

CROSS-REFERENCE TO RELATED APPLICATIONS

The present patent application is a national phase application of International Application No. PCT/ES2017/070339, filed May 22, 2017, which claims priority to Spanish Patent Application No. P201630658, filed May 20, 2016, the disclosures of which are incorporated herein by reference.

INCORPORATION BY REFERENCE

The content of the ASCII text file of the sequence listing named "sequence_listing_PCT1861_52", which is 17.2 kb in size, was created on and electronically submitted via EFS-Web Jun. 11, 2019, is incorporated herein by reference in its entirety.

The present invention relates to the field of bioproducts, preferably biofuels, and more particularly, the improvement of cellulolytic cocktails produced by the modified host cells that express and/or secrete a lower diversity of cellulolytic enzymes, the enzymatic cocktails produced from said host cells, and the use of said host cells and said enzymatic cocktails in the production of bioproducts, preferably bioethanol, from biomass.

STATE OF THE ART

Biofuels are an attractive alternative to fossil fuels and can be produced by fermentation of monomeric sugars derived from starch or cellulose and hemicellulose.

Plant biomass provides a potential complete energy source in the form of sugars that can be used for numerous industrial and agricultural processes, and it is, therefore, a significant renewable resource for the generate fermentable sugars that may give the result of commercially valuable end products, such as biofuels. However, the enormous potential energy of these carbohydrates is currently underused as the sugars are forming part of complex polymers and they are not easily accessible for fermentation.

Any plant biomass can be considered as raw material for the production of biofuels such as herbaceous crops, other agricultural residues or even solid urban waste. These materials mainly comprise cellulose and hemicellulose. Once the cellulose and hemicellulose turn into glucose and xylose, respectively, by means of an enzymatic hydrolysis process, these compounds are easily fermented by other organisms to ethanol. In this way, the greater amount of complex sugars that remains at the end of the hydrolytic process, the smaller the yield of the ethanol production shall be at the end of the fermentation process. Therefore, an area of research intended to decrease costs and enhance the yield of biofuel production methods centres on improving the efficiency of the cellulolytic enzymes, and the enzymatic cocktails comprising said enzymes and which can be used to generate fermentable sugars from biomass.

Due to the complexity of the biomass, its conversion in monomeric sugars involves the action of various types of enzymes with various enzymatic activities, which digest cellulose, hemicellulose, and other complex polymers present in the biomass. After cellulose, hemicellulose is the second most abundant fraction available in nature. Both cellulose and hemicellulose may be previously treated, mechanically, chemically, enzymatically or otherwise, to increase their susceptibility to hydrolysis. After this pretreatment process a saccharification stage takes place, which is an enzymatic process whereby complex carbohydrates degrade in their monosaccharide components. The objective of any saccharification technology is to alter or eliminate the structural and composition impediments for hydrolysis with the aim of improving the rate of enzymatic hydrolysis and increasing the yields of fermentable sugars from the biomass, comprising mainly, cellulose and hemicellulose (N. Mosier et al., 2005, Bioresource Technology 96, 673-686). A fermentation process is performed after this saccharification stage.

Individual enzymes have demonstrated only partial digestion of cellulose and hemicellulose and, therefore, concerted action is required of all or at least several of the enzymes called "cellulases or cellulolytic enzymes" to complete the conversion of the different complex polymers, specifically, cellulose and hemicellulose, to monomeric sugars. Cellulases (1,4-beta-D-glucan-4-glucohydrolase, EC 3.2.1.4) comprise at least three enzymatic activities, endo-β-glucanases (EC 3.2.1.4), exo-β-glucanases or cellobiohydrolases (EC 3.2.1.91) and β-glucosidases (EC 3.2.1.21), of which their synergic action has been demonstrated in cellulose hydrolysis (Woodward, J. 1991, Bioresource Technology Vol 36, page 67-75). In addition to these three activities, today others of equal relevance are recognised, such as, xylanases (E.C. 3.2.1.8), beta-xylosidases (E.C. 3.2.1.37) and polysaccharide monooxygenases (also called PMO, AA9, glycosyl-hydrolase of family 61 or GH61).

The hydrolytic efficiency of a multienzyme complex, formed by a wide variety of cellulolytic enzymes, in the cellulosic saccharification process depends both on the properties of the individual enzymes and on the ratio of each enzyme in the complex.

Consequently, cellulases have turned into biocatalysts due to their complex nature and their extensive industrial applications. Today, considerable attention is paid to the production of cellulases and to the advances in research, especially in the direction of improvement of the process economy of several industries with the aim of obtaining enzymatic compositions which have greater activity and better cellulolytic properties. Thus, the majority of efforts in the present technical field have been directed at the generation of microorganisms that express improved enzymatic cocktails thanks to the overexpression of one or more genes which code for specific cellulolytic enzymes, with it being possible that said genes are both homologous and heterologous. This overexpression may occur by any method known in the state of the art, one of them being expression under the control of strong expression signals, which gives rise to a greater production of that or those enzymes within the enzymatic cocktail (US20080194005A1). Numerous host cells used for the expression of heterologous genes have been disclosed in the state of the art, such as the bacteria *Escherichia coli*, and its transformation methods. In this context, numerous fungal systems have also been developed, for example, *Aspergillus niger, Aspergillus awamori, Aspergillus nidulans*, among others. However, for various reasons, many of these recombinant microorganisms have not met wide acceptance or use. Among the recombinant microorganisms that are currently used for the production of proteins or enzymes, those of the following genuses stand out: *Candida, Kluyveromyces, Pichia, Saccharomyces, Schizosaccharomyces, Yarrowia, Acremonium, Agaricus, Alternaria, Aspergillus, Aureobasidium, Botryosphaeria, Ceripo-* riopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella or Xylaria.

In general terms, a host cell producer of an ideal cellulolytic cocktail must fulfil a large number of criteria, such as, efficiently using the medium, producing the polypeptide(s) or the protein(s) of interest with a high yield, where applicable, be capable of secreting the protein(s) or the polypeptide(s) or the enzymatic compositions efficiently, be able to use a wide range of expression regulation elements guaranteeing in this way an easy application and versatility, allowing the use of easily detectable markers which are cheap to use and produce stable transformers.

In short, it is desirable to generate microorganisms which express an optimum enzymatic cocktail that improves the yield and efficiency of the biomass degradation process. It would also be desirable, with a view to making the process more economical, that the optimum or improved enzymatic cocktail would allow the use of a smaller amount of enzymes within the cocktail, for the production thereof, or improved production yields of fermentable sugars in said biomass degradation processes.

DESCRIPTION OF THE INVENTION

The present invention discloses a modified host cell capable of secreting an optimised enzymatic composition which has a greater cellulolytic capacity with respect to the composition produced by the unmodified parental or wild-type cell.

The modification carried out in the host cell of the invention is aimed at decreasing the expression and/or secretion of at least one, or more than one, of the cellulolytic enzymes that said host cell homologously expresses and which form part of the enzymatic composition said cell secretes and expresses, with the condition that the cellulolytic enzyme(s) whereof the expression and/or secretion are decreased are those cellulolytic enzymes which have a lower cellulolytic activity in relation to the cellulolytic activity that other cellulolytic enzymes of its same family included in the cocktail have.

The industrial conditions wherein enzymatic cocktails are used rather more controlled and predefined, with respect to the environmental conditions wherein the organisms that produce them are found. For said reason, to perform biomass hydrolysis on an industrial scale, it does not require the presence of a wide enzymatic diversity, which translates into redundant enzymatic activities, which do not improve process yields, since in industrial reaction conditions only a few of the cellulolytic enzymes are going to be capable of contributing to the reaction efficiency. Expression of the other redundant enzymes and with limited catalytic activity is, therefore, undesirable in those industrial conditions. Hence, in the present invention, with a fewer number of inefficient enzymes (hereinafter, "non-contributory" enzymes or cellulases) and a larger proportion of the efficient ones (hereinafter, "contributory" enzymes or cellulases), it is possible to improve the yield and the efficiency of the biomass degradation process in comparison with other cocktails with greater diversity but lower efficiency. This greater efficiency relates to the use of a lower diversity of enzymes in the enzymatic cocktail, for the production of better yields (greater production of fermentable sugars, such as glucose) in said biomass degradation processes.

Therefore, from an economic standpoint of the industrial biomass degradation processes wherein the enzymatic composition described in the present invention is used, said composition enables producing better yields with a lower enzyme diversity in the enzymatic cocktail, so that it increases the efficiency of the biomass degradation process, since there is a greater representation of contributory enzymes (FIG. 1).

The objective of the present invention is to reduce said enzymatic diversity by means of the reduction of the expression and/or secretion of one or several cellulolytic enzyme(s) which has/have a lower cellulolytic efficiency with respect to that shown by other cellulolytic enzymes of their same family within the cocktail, to thus obtain an enzymatic composition that has a greater concentration of those cellulolytic enzymes which have a greater efficiency and show an increase in the efficiency of the biomass degradation process.

Another of the advantages obtained with the host cells of the invention and with the enzymatic compositions produced from said host cells of the invention, is that, since said compositions comprise the cellulolytic enzyme(s) which has/have a greater cellulolytic efficiency, it requires a lower diversity of enzyme(s) in the enzymatic composition of the invention, for the production of better production yields of fermentable sugars in comparison with those that have been produced using other known compositions which have a broad enzymatic diversity and disclosed in the state of the art for the same purpose.

Therefore, the present invention represents a solution to the need for providing a microorganism which expresses an optimised mixture or cocktail of cellulolytic enzymes, capable of improving the efficiency of the cellulolytic process of the biomass or saccharification, by means of the decreased expression and/or secretion of non-contributory cellulolytic enzymes which have less efficiency with respect to other contributory cellulolytic enzymes and, as a consequence, it requires a lower enzymatic diversity or in the enzymatic cocktail comprising contributory enzymes, to obtain better yields (greater amounts of fermentable sugars released). Thus, the enzymatic composition expressed and/or secreted by the modified host cells of the invention has a greater cellulolytic efficiency and a greater concentration of contributory cellulolytic enzymes which are selected from those that have a greater cellulolytic efficiency within the group of enzymes that form part of the enzymatic diversity of the cocktail. This greater concentration of contributory cellulolytic enzymes in the enzymatic composition of the invention is a consequence of the lower expression and/or secretion of the non-contributory cellulolytic enzymes, since the contributory cellulolytic enzymes occupy the space left, in terms of quantity present in the enzymatic composition, by the non-contributory enzymes eliminated (FIG. 1).

Thus, the present invention discloses a modified host cell which produces a less diverse enzymatic cocktail, as it has a reduced expression and/or secretion of at least one non-contributory cellulolytic enzyme with respect to the expression of the same non-contributory cellulolytic enzyme in a parental or wild-type or unmodified host cell. Additionally, the modified host cell of the invention has a greater cellulolytic efficiency, of transformation of the cellulosic material in fermentable sugars, than a non-genetically modified parental or wild-type host cell.

Said modified host cell, as defined in the present invention, may additionally present an increase in the expression of at least one contributory cellulolytic enzyme with respect to the expression of said contributory cellulolytic enzyme(s) in a non-genetically modified wild-type host cell. The contributory cellulolytic enzyme(s) whose expression may be increased in the host cell of the invention, may preferably be selected from homologous contributory cellulolytic enzyme(s) and/or heterologous contributory cellulolytic enzyme(s).

The inventors have demonstrated that a lower expression and/or secretion of non-contributory cellulolytic enzymes in host cells gives rise to the expression and/or secretion of an enzymatic composition which has an increase in the concentration (or a greater representation) of contributory cellulolytic enzymes which have a greater efficiency than non-contributory cellulolytic enzymes, which translates into the use of a lower diversity of cellulolytic enzymes in the industrial biomass degradation processes and, therefore, also into an increase in the efficiency of saccharification process and, finally in the overall yield of the bioproduct production processes, preferably biofuel, since, as previously mentioned, a lower enzymatic diversity is required to obtain a greater production of fermentable sugars at the end of the hydrolysis or saccharification process.

Therefore, a first aspect of the present invention is related to a modified host cell which has a reduced expression and/or secretion of at least 10% in at least one of the non-contributory cellulolytic enzymes with respect to the expression and/or secretion percentage of said non-contributory cellulolytic enzyme in a parental or wild-type host cell. Hereinafter and throughout the present document, this first aspect of the invention shall be called "host cell of the invention".

In some preferred embodiments, the host cell of the invention has been genetically modified to reduce the expression and/or secretion of at least one non-contributory cellulolytic enzyme by approximately at least 1%, approximately at least 2%, approximately at least 3%, approximately at least 4%, approximately at least 5%, approximately at least 10%, approximately at least 15%, approximately at least 20%, approximately at least 25%, approximately at least 30%, approximately at least 35%, approximately at least 40%, approximately at least 45%, approximately at least 50%, approximately at least 55%, approximately at least 60%, approximately at least 65%, approximately at least 70%, approximately at least 75%, approximately at least 80%, approximately at least 85%, approximately at least 90%, approximately at least 95%, approximately at least 100% with respect to the expression of said non-contributory cellulolytic enzymes in a parental or wild-type host cell. In a more preferred embodiment, the host cell of the invention has a reduction of 100% of the expression and/or secretion of at least one non-contributory cellulolytic enzyme with respect to a parental or wild-type host cell.

For the purposes of the present invention, the terms "parental or wild-type host cell" can be equally used and relate to that host cell that has not been modified to have a reduced expression and/or secretion of one or more than one non-contributory cellulolytic enzyme as disclosed in the present invention. Preferably, the parental or wild-type cell of the present invention is *Myceliophthora thermophila*, more preferably *M. thermophila* C1.

In particular embodiments, the host cells are modified to delete, totally or partially inhibit or totally or partially silence, coding sequences of non-contributory cellulolytic enzymes or, otherwise, totally or partially eliminate the expression of one or more non-contributory cellulolytic enzymes.

Additionally, the host cells of the invention, in addition to having a reduced expression and/or secretion of at least one non-contributory cellulolytic enzyme, may undergo other genetic modifications with the purpose of having characteristics that improve protein secretion, protein stability or other properties desirable for the expression and/or secretion of one or more contributory cellulolytic enzymes.

In a preferred embodiment, the expression and/or secretion of one or more non-contributory cellulases is totally or partially decreased, reduced or inhibited, which leads to a greater representation of the cellulases of interest, which in the present invention relate, preferably, to contributory cellulolytic enzymes, in the enzymatic cocktail produced from said cell.

The genetic modification of the cell of the invention may be achieved by genetic engineering techniques or using classic microbiological techniques such as chemical or UV mutagenesis and subsequent selection. It is possible to use a combination of recombinant modification and classic selection techniques to produce the organism of interest. Using recombinant technology, the nucleic acid molecules can be inserted, deleted, disrupted, silenced, inhibited or modified, so that a reduced or zero expression occurs of the non-contributory cellulolytic enzymes, which is associated to a high yield of the secretion of the contributory cellulolytic enzymes within the organism or in the culture. In a genetic engineering approach, homologous recombination may be used to induce modifications of genes chosen as target specifically choosing as target a gene in vivo to suppress expression of the coded protein. In an alternative approach, it is also possible to use antisense RNAi to decrease or inhibit gene expression. Thus, in a preferred embodiment, the host cells of the invention are modified to eliminate at least one gene which codes for a non-contributory cellulase or alternatively, decrease or eliminate the expression of one or more non-contributory cellulases. In some embodiments, the expression of one or more non-contributory cellulases is decreased, inhibited, silenced or deleted to increase the production or the presence in the enzymatic cocktail secreted by the modified host cell of other cellulases of interest, such as contributory cellulases.

In another preferred embodiment, the secretion of one or more non-contributory cellulases may be inhibited, decreased or cancelled out. Alterations in the secretion of the cellulolytic enzymes in the host cell of the invention may affect both secretion of the non-contributory cellulase(s) and the general enzyme secretion system that specifically inhibits, decreases or cancels out the secretion of the non-contributory cellulase(s). Using recombinant technology, the nucleic acid molecules that code for the signal peptide or sequences that allow the secretion of the non-contributory cellulolytic enzyme(s) may be inserted, deleted, disrupted, silenced, modified, inhibited, so that a decreased or zero secretion of the non-contributory cellulolytic enzymes occurs. In a genetic engineering approach, the homologous recombination can be used to induce modifications in the secretion system of non-contributory cellulolytic enzymes. Thus, in a preferred embodiment, the host cells of the invention are modified to decrease or cancel out the secretion of at least one non-contributory cellulase.

For the purposes of the present invention, the term "expression" or "gene expression" relates to the transcription of a specific gene or specific genes or specific genetic construction in mRNA with the subsequent translation of the latter in a protein. It additionally includes the secretion of the protein to the outside of the cell.

For the purposes of the present invention, the term "secretion" relates to the transport of a protein from the inside of a cell to the outside. For the purposes of the present invention, the term secretion make reference, preferably, to the secretion of enzymes with cellulolytic activity, which due to the effect of this transport appear in the enzymatic cocktail produced by said cell.

For the purposes of the present invention, the terms "increase in the expression" or "overexpression" may be equally used through the present document and relate to any form of expression which is additional to or greater than the original expression level in a parental or wild-type cell. The methods for increasing gene or gene product expression are well-documented in the state of the art and include, for example, overexpression driven by appropriate promoters, the use of transcription enhancers or translation enhancers. Isolated nucleic acids may also serve as promoters or enhancers and can be inserted in an appropriate position, in a non-heterologous manner of a polynucleotide with the aim of regulating by increasing the expression of a nucleic acid which codes for the polypeptide of interest. For example, endogenous promoters may be altered in vivo by mutation, deletion, and/or substitution, or isolated promoters may be inserted in a polynucleotide sequence that codes for a gene of interest to control the expression thereof. For the purposes of the present invention, the aim is that these terms cover the increase in the expression of both homologous and heterologous enzymes. In some embodiments, the increase in expression includes a high transcription rate and/or a level of the gene which is also high in comparison with the homologous transcription rate of said gene. In some other embodiments, a heterologous gene is inserted in a host cell to induce an increase in expression of a gene which codes for a homologous enzyme. In some embodiments, the heterologous gene is a gene that has been modified to increase the expression of the gene product. In some embodiments, the term also covers the secretion of the polypeptide from a cell.

For the purposes of the present invention, the terms "endogenous" or "homologous" relate to both genes and proteins, which are naturally found in a host cell, i.e. without any human intervention. Additionally, said terms also make reference to those same genes or proteins which, once isolated from the organism, may be reinserted (transgene) by means of genetic engineering.

For the purposes of the present invention, the term "decrease", "reduction", "suppression", "inhibition", "deletion", "silencing", "elimination", relate to a fall in the expression level of a gene and/or secretion of the protein with respect to the original expression level of the same gene and/or secretion of the protein in the parental or wild-type genotype. For the purposes of the present invention, the decrease, elimination, reduction, suppression, inhibition, deletion, silencing or inhibition, of the expression and/or secretion in rising order of preference is of at least 10%, 20%, 30%, 40%, 50%, 60%, 70%, 80%, 85%, 90%, 95%, 96%, 97%, 98%, 99% or 100%, reduced in comparison with the expression in the parental or wild-type host cells.

A person skilled in the art knows the different routine tools and techniques for the elimination, reduction, suppression, deletion, silencing or inhibition of the expression of a gene or protein. For the purposes of the present invention, the following serve as example: the cloning of a target gene or genes in inverted repetition form (partially or totally), loss, substitution or blocking of genetic material that results in a complete or partial interruption of the DNA sequence that composes the gene, alterations of the promotor or any other reduction in the transcription level, alteration of the expression of regulatory proteins, gene silencing (dsRNA, siRNA, etc.), modification of the translation initiation sequence, alteration of the reading, where appropriate changes in secretion (alterations of the signal peptide, etc.), mutagenesis, etc. In some embodiments, gene silencing is preferred. In other embodiments, the partial suppression or elimination of the gene is preferred. In other embodiments, the complete or almost complete suppression of the gene sequence is preferred.

A person skilled in the art knows the different routine tools and techniques for the elimination, reduction, suppression or inhibition of the secretion of a protein. For the purposes of the present invention, the following serve as an example: the directed or random genetic modification of the signal sequences (signal peptide) which allow the secretion of a protein or the directed or random genetic modification of the secretion system of the host cell in itself. Genetic modifications may consist of a loss of regions, modifications, substitutions, integrations, alterations, silencing, alteration of the reading frame, etc.

As used here, the term "recombinant" relates to a polynucleotide or polypeptide which is not naturally produced in a host cell. In some embodiments, the "recombinant cells" express genes that are not found identically within the native or wild-type form (i.e. not recombinant) of the cell and/or express native genes which their expression would otherwise be increased, decreased or cancelled out due to deliberate human intervention. Recombinant cells contain at least one recombinant polynucleotide or polypeptide. A nucleic acid construction comprising the nucleic acid and the elements necessary for its expression, the nucleic acid (for example, a polynucleotide), cell or polypeptide are here called "recombinant" when it is of non-natural, artificial or processed origin.

The term "biomass" relates in the present invention to the biodegradable fraction of the products, residues and waste of biological origin from agriculture (including plant substances, such as crop waste and animal substances), forest industries (such as wood resources) and related industries which include fisheries and aquaculture, and the biodegradable fraction of industrial and urban waste, such as solid urban water or paper waste, and energy crops. In a preferred embodiment, the biomass is straw or the organic fraction of urban solid waste. In a more preferred embodiment, the biomass is plant biomass, more preferably selected from the list consisting of: biomass rich in fermentable sugars, such as sugarcane, starch biomass, for example, cereal grains, corn straw, wheat straw, barley straw, sorghum straw, sugarcane straw, scrub, trunks, branches and leaves.

The predominant polysaccharide in the primary cell wall of biomass is cellulose, the second most abundant is hemicellulose, and the third is pectin. The secondary cell wall, produced after the cell has stopped growing, also contains polysaccharides and is reinforced by means of polymeric lignin covalently cross-linked with hemicellulose. Cellulose is a homopolymer of anhydrocellobiose and in this way is a linear β-(1,4)-D-glucan, whilst hemicellulose includes a variety of compounds such as xylans, xyloglucans, arabinoxylans and mannans in complex branched structures with a range of substitutes. Although generally polymorphous, cellulose is found in the plant tissue mainly as an insoluble crystalline matrix of parallel glucan chains. Hemicelluloses normally bond via hydrogen bonds to cellulose, and to other hemicelluloses, which assists in stabilizing the cell wall matrix.

For the purposes of the present invention, the term "cellulose" relates to a linear polysaccharide comprising hundreds to thousands of D-glucose units bound by β-(1,4) bonds. This polysaccharide is also known as β-(1,4) glucan.

The term "cellulolytic enzyme or cellulase" relates to a category of enzymes which can degrade complex polymers, such as, cellulose and/or hemicellulose (β-1,4-glucan or β-D-glycosidic bonds) to shorter oligosaccharides, such as, cellobiose and/or glucose and xylobiose and/or xylose, respectively. The following groups are preferably found within said category of enzymes: 1,4-β-D-glucan glucohydrolase ("endoglucanase" or "EG"); 1,4-β-D-glucan cellobiohydrolase ("exoglucanase", "cellobiohydrolase", or "CBH"); β-D-glucoside glucohydrolase ("β-glucosidase", "cellobiase" or "BGL"), endoxylanases or xylanases ("Xyl"), beta-xylosidases ("beta-Xyl") and polysaccharide monooxygenases ("PMO"). Endoglucanases break internal bonds and alter the crystalline structure of cellulose, exposing individual cellulose polysaccharide chains ("glucans"). Cellobiohydrolases gradually shorten the glucan molecules, mainly releasing cellobiose units (a glucose dimer bound in water-soluble β-1,4), in addition to glucose, cellotriose and cellotetraose. β-glucosidases fractionate cellobiose in glucose monomers. Xylanases catalyse the random hydrolysis of polymeric xylan, polymeric pectin or hemicellulose which contains xylose residues and which gives the result of the formation of sugar oligomers which contain xylose and/or monomeric xylose residues. Beta-xylosidases are enzymes with 4-β-D-xylan xylohydrolase activity catalysing the reaction from the xylose oligomers, including xylobiose, finally releasing D-xylose. PMO are metalloproteins with endocellulolytic activity which act with a different mechanism to that performed by endoglucanases, since they break cellulose chains by oxidation of their glucose monomers in carbons 1, 4 and/or 6.

The term "efficiency" of an enzyme, enzyme group or enzymatic composition, relates to the catalytic activity of the enzyme, enzyme group or enzymatic composition, in appropriate conditions wherein the enzyme converts specific polymeric or artificial substrates into specific oligomeric or monomeric products. Preferably, a "greater efficiency" or "better efficiency" of the enzymes of the invention or of the enzymatic cocktail of the invention, relates to the production of the same, or preferably greater quantity of fermentable sugars produced at the end of the hydrolytic process (i.e. the same or greater yield), with a lower diversity of cellulolytic enzymes present in the cocktail, with respect to an enzymatic cocktail produced from a wild-type or parental host cell.

The term "contributory cellulolytic enzymes" relates to those cellulases within the diversity of cellulases present in enzymatic cocktails, such as preferably, endoglucanases, cellobiohydrolases, β-glucosidases, β-xylosidases, xylanases, polysaccharide monooxygenases, among others, which have a cellulolytic activity so that on being eliminated from an enzymatic cocktail the yield is reduced in terms of release of fermentable sugars per unit of mass. In a preferred embodiment, a contributory cellulolytic enzyme of any of the families or cellulolytic activities described in the present invention may be selected from a homologous or heterologous cellulase.

The term "non-contributory cellulolytic enzyme" relates to those cellulases within the diversity of the cellulases present in enzymatic cocktails, such as preferably, endoglucanases, cellobiohydrolases, β-glucosidases, β-xylosidases, xylanases, polysaccharide monooxygenases, among others, which have a cellulolytic activity so that when they are eliminated or reduced from an enzymatic cocktail, the efficiency thereof is improved. In a preferred embodiment, a non-contributory cellulolytic enzyme of any of the families or cellulolytic activities disclosed in the present invention may be preferably selected from a homologous or heterologous cellulase. In a preferred embodiment, the non-contributory cellulase of the invention is a homologous cellulase.

The term "cellobiohydrolase", as used in the present document, relates to a protein of class E.C. 3.2.1.91, which catalyses the hydrolysis of the polymeric cellulose to cellobiose by means of an exoglucanase activity, sequentially releasing cellobiose molecules from the reducing or non-reducing ends of the cellulose.

The term "endoglucanase", "EG" or "Eg", as used in the present document, relates to a group of cellulase enzymes classified as E.C. 3.2.1.4. These enzymes hydrolize the internal glycosidic β-1,4 bonds of the cellulose.

The term "beta-glucosidase", as used in the present document, relates to a group of cellulase enzymes classified as EC 3.2.1.21. These enzymes catalyse the hydrolysis of sugar oligomers, including, but without being limited to, the cellobiose or glucose dimer, with the release of a corresponding sugar monomer, used, but without being limited, for ethanol synthesis. The beta-glucosidase enzyme acts on the β-(1,4) bonds which bind two glucose or substituted glucose molecules (i.e. the disaccharide cellobiose). It is an exocellulase with specificity for a variety of beta-D-glucoside substrates. It catalyses the hydrolysis of terminal non-reducing residues in beta-D-glucosides with glucose release.

The terms "endoxylanase" or "xylanase", as used in the present document, relate to a group of enzymes (EC 3.2.1.8) which catalyse the endohydrolysis of 1,4-β-D-xylosidic bonds in xylans. This enzyme may also be called endo-1, 4-β-xylanase or 1,4-β-D-xylan xylanhydrolase.

The term "beta-xylosidase", as used in the present document, relates to a group of enzymes (EC 3.2.1.37) which catalyse the hydrolysis of 1,4-β-D-xylans, to eliminate successive D-xylose residues from the non-reducing ends. This enzyme may also be called xylan 1,4-β-xylosidase, 1,4-β-D-xylan xylohydrolase, exo-1,4-β-xylosidase or xylobiase.

The terms "polysaccharide monooxigenase", "PMO", "Glycosyl-hydrolase of family "61" or "GH61" or "AA9" relate to a group of enzymes, originally classified within the GH61 protein family, since they have GH61 or PMO activity, and which when they are included in a saccharification reaction it results in a greater quantity (greater yield) of one or more soluble sugars (for example, glucose) in comparison with the saccharification reaction carried out under the same conditions but in the absence of protein GH61. The members of this enzyme family act as copper monooxigenases which catalyse the breakage of the cellulose chains by means of an oxidative mechanism at the level of several carbons (C1, C4 and/or C6), releasing cellodextrins (Langston et al. Applied and Environmental Microbiology, 2011, 77:7007-7015).

The term "identity" and "% identity" relate to the proportion of nucleic acid or amino acid residues which are identical among two sequences of nucleic acids or amino acids that are being compared. It is possible to determine the degree of identity via the Clustal method, Wilbur-Lipman method, the GAG program, which includes GAP, BLAST or BLASTN, EMBOSS Needle and FASTA. Furthermore, it is possible to use the Smith Waterman algorithm with the aim of determining the degree of identity between two sequences. In preferred embodiments of the present invention, the nucleotide and peptide sequences described comprise at least at least approximately 60%, at least approximately 65%, at least approximately 70%, at least approximately 75%, at least approximately 80%, at least approximately 85%, at least approximately 88% identity, at least approximately 89%, at least approximately 90%, at least approximately 91%, at least approximately 92%, at least approximately 93%, at least approximately 94%, at least approximately 95%, at least approximately 96%, at least approximately 97%, at least approximately 98%, at least approximately 99% or 100% identity on a reference sequence, when they are compared and aligned for a maximum correspondence on a window of comparison, or designated region depending how they are measured using the above algorithms.

In another preferred embodiment, the host cells of the invention as disclosed here, may additionally, have an increase of at least 1% of the expression and/or secretion of at least one contributory cellulolytic enzyme with respect to the percentage of the expression and/or secretion of the same contributory cellulolytic enzyme(s) in a parental or wild-type host cell.

In a preferred embodiment, the host cells of the invention, to have an increase in the expression of at least one of the contributory cellulolytic enzymes, may undergo genetic modifications with the aim of improving the expression and secretion of at least one of said enzymes, the stability thereof or other desirable properties for the induction of the increase in the expression and/or secretion of the contributory cellulolytic enzyme(s). In more particular embodiments, the host cells are additionally genetically modified to increase the expression or insert more than one copy of the coding sequences of contributory cellulolytic enzymes which may be both homologous and heterologous. In a preferred embodiment, the overexpression of one or more contributory cellulases is carried out to increase the production or proportion of contributory cellulases. In other even more particular embodiments, the host cells of the invention are additionally characterised in that they have an increase in the expression of at least one of the contributory cellulolytic enzymes, said enzymes also have greater cellulolytic activity. The genetic modification for the production of said characteristics in the strains of the invention can be achieved by genetic engineering techniques or using classic microbiological techniques such as chemical or UV mutagenesis and subsequent selection. A combination of recombinant modification and classic selection techniques can be used to produce the organism of interest. Using recombinant technology, the nucleic acid molecules can be inserted, overexpressed or modified, so that a high yield is produced from the secretion of contributory cellulolytic enzymes within the organism or in the culture. In a genetic engineering approach, the homologous recombination can be used to induce modifications of genes chosen as target, specifically choosing an in vivo gene as target to increase expression of the coded protein.

In some preferred embodiments, the host cell disclosed in the present invention has been genetically modified to overexpress at least one of the contributory cellulolytic enzymes by approximately at least 1%, approximately at least 5%, approximately at least 10%, approximately at least 20%, approximately at least 25%, approximately at least 30%, approximately at least 35%, approximately at least 40%, approximately at least 45%, approximately at least 50%, approximately at least 55%, approximately at least 60%, approximately at least 65%, approximately at least 70%, approximately at least 75%, approximately at least 80%, approximately at least 85%, approximately at least 90%, approximately at least 95%, approximately at least 96%, approximately at least 97%, approximately at least 98%, approximately at least 99%, approximately at least 100% with respect to the expression of said contributory cellulolytic enzymes in a wild-type host cell.

In another preferred embodiment, the host cells of the invention are characterised in that they have overexpression of at least one of the contributory cellulolytic enzymes selected by means of the method described in the present invention.

In another more preferred embodiment, the host cells of the invention are characterised in that the contributory cellulases may be derived from the host cell of the invention (homologous) or from other cellulolytic enzyme-producing microorganisms different from the host cell of the invention (heterologous). They may also be produced in a natural or recombinant manner.

In another more preferred embodiment, the host cells of the invention are characterised in that the contributory cellulolytic enzyme that may increase its expression is preferably a cellobiohydrolase. In a more preferred embodiment, said cellobiohydrolase is preferably any cellobiohydrolase which has the greatest efficiency within its family.

In another more preferred embodiment, the host cells of the invention are characterised in that the contributory cellulolytic enzyme which may increase its expression is preferably an endoglucanase. In an even more preferred embodiment, the endoglucanase is preferably any endoglucanase which has the greatest efficiency within its own family. In another more preferred embodiment, the preferred endoglucanase is endoglucanase 2. In another more preferred embodiment, endoglucanase 2 preferably comprises a sequence which has at least 60% identity with SEQ ID NO: 6, and optionally coded by a nucleotide sequence comprising a sequence which has at least 60% identity with SEQ ID NO: 5. Even more preferred, endoglucanase 2 is endoglucanase 2 comprising SEQ ID NO: 6, optionally coded by the nucleotide sequence comprising SEQ ID NO: 5.

In another more preferred embodiment, the host cells of the invention are characterised in that the contributory cellulolytic enzyme which may increase its expression is preferably a beta-glucosidase. In an even more preferred embodiment, the beta-glucosidase is preferably any beta-glucosidase which has the greatest efficiency within its own family.

In another more preferred embodiment, the host cells of the invention are characterised in that the contributory cellulolytic enzyme which may increase its expression is preferably an endoxylanase. In an even more preferred embodiment, the endoxylanase is preferably any endoxylanase which has the greatest efficiency within its own family.

In another more preferred embodiment, the host cells of the invention are characterised in that the contributory cellulolytic enzyme which may increase its expression is preferably a beta-xylosidase. In an even more preferred embodiment, the beta-xylosidase is preferably any beta-xylosidase which has the greatest efficiency within its own family.

In another more preferred embodiment, the host cells of the invention are characterised in that the contributory cellulolytic enzyme which may increase its expression is preferably a polysaccharide monooxygenase. In an even more preferred embodiment, the polysaccharide monooxygenase is preferably any polysaccharide monooxygenase which has the greatest efficiency within its own family.

In an even more preferred embodiment, the host cell of the invention is characterised in that it has a reduced expression of a non-contributory homologous endoglucanase which has at least 60% identity with endoglucanase 6 comprising SEQ ID NO: 2, optionally coded by a nucleotide sequence which has at least 60% identity with endoglucanase 6 comprising SEQ ID NO: 1. Even more preferred, endoglucanase 6 is endoglucanase 6 comprising SEQ ID NO: 2, optionally coded by the nucleotide sequence comprising SEQ ID NO: 1. Preferably, the reduced expression relates to deletion of the gene which codes for endoglucanase 6.

In an even more preferred embodiment, the host cell of the invention is characterised in that it has a reduced expression of a homologous non-contributory polysaccharide monooxygenase which has at least 60% identity with polysaccharide monooxygenase 09768 comprising SEQ ID NO: 4, optionally coded by a nucleotide sequence which has at least 60% identity with polysaccharide monooxygenase 09768 comprising SEQ ID NO: 3. Even more preferred, polysaccharide monooxygenase 09768 is polysaccharide monooxygenase 09768 comprising SEQ ID NO: 4, optionally coded by the nucleotide sequence comprising SEQ ID NO: 3. Preferably, the reduced expression relates to deletion of the gene which codes for polysaccharide monooxygenase 09768.

In another preferred embodiment, the host cell of the invention is characterised in that it has a reduced expression of a homologous non-contributory endoglucanase which has at least 60% identity with endoglucanase 6 comprising SEQ ID NO: 2, optionally coded by a nucleotide sequence which has at least 60% identity with endoglucanase 6 comprising SEQ ID NO: 1 and a reduced expression of a homologous non-contributory polysaccharide monooxygenase which has at least 60% identity with polysaccharide monooxygenase 09768 comprising SEQ ID NO: 4, optionally coded by a nucleotide sequence which has at least 60% identity with polysaccharide monooxygenase 09768 comprising SEQ ID NO: 3.

In another even more preferred embodiment, the host cell of the invention is characterised in that it has a reduced expression of endoglucanase 6 of SEQ ID NO: 2 and polysaccharide monooxygenase 09768 of SEQ ID NO: 4. Preferably, the reduced expression of endoglucanase 2 and polysaccharide monooxygenase 09768 relates to deletion of the genes which code for said enzymes.

As described in the present document, the "host cell" includes any type of cell that is susceptible to transformation, transfection, transduction and similar, with one or several constructions of nucleic acid or expression vector comprising a polynucleotide which codes for the cellulases described here, both contributory cellulases and non-contributory cellulases. The host cell may be a eukaryote cell or prokaryote cell.

In a particular embodiment, the host cell is a prokaryote cell which is preferably selected from the group of bacteria of the genuses *Bacillus, Clostridium, Escherichia, Klebsiella, Pseudomonas, Streptomyces, Thermoanaerobacterium* or *Zymomonas*.

In another particular embodiment, the host cell is a eukaryote cell which is preferably selected from the group of fungi of the genuses *Candida, Kluyveromyces, Pichia, Saccharomyces, Schizosaccharomyces, Yarrowia, Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella* or *Xylaria*.

In an even more preferred embodiment, the host cell of the invention is any strain of the species *Myceliophthora thermophila*. In an even more preferred embodiment, the host cell of the invention is the C1 strain of *Myceliophthora thermophila*.

It shall be understood that for the aforementioned genuses and species, the invention covers perfect and imperfect states, and other taxonomic equivalents, e.g. anamorphs, with respect to the name of the species whereby they are known. Persons skilled in the art shall easily recognise the identity of the suitable equivalents. For example, *Myceliophthora thermophila* is equivalent to *Chrysosporium lucknowense*.

Another aspect of the present invention relates to an enzymatic cocktail produced by the host cells of the invention. Said enzymatic cocktail comprises, at least, the contributory cellulolytic enzymes as defined above and which are secreted by the host cells of the invention, so that it will lack at least one of the non-contributory cellulolytic enzymes as defined above. Hereinafter and throughout the present document, this cocktail shall be called "cocktail of the invention". Preferably, in a particular embodiment, the enzymatic cocktail referred to in the present document comprises the contributory cellulolytic enzymes as defined above and lacks enzyme activity of, at least, one cellulase with endoglucanase activity, preferably, endoglucanase 6 (Eg6), and/or at least one cellulase with polysaccharide monooxygenase activity, preferably PMO-09768.

The cocktail of the invention may be additionally supplemented by adding other accessory or additional enzymes, which may be both homologous and heterologous, and which are also characterised in that their specific enzymatic activity may not be replaced by any of the enzymatic activities that the contributory cellulolytic enzymes present. Said accessory or additional enzymes are selected from any of the following: aminopeptidases, amylases, carbohydrases, carboxypeptidases, catalases; chitinases, cutinases, cyclodextrin glycosyltransferase, deoxyribonucleases, esterases, alpha-galactosidase, beta-galactosidase, glucoamylase, alpha-glucosidases, haloperoxidases, invertases, laccases, lipases, mannosidases, oxidases, oxidoreductases, pectinolytic enzymes, peptidoglutaminases, peroxidases, proteases, phytases, polyphenol oxidases, proteolytic enzymes, ribonucleases, transglutaminases, any combinations thereof, provided that it does not present the non-contributory cellulolytic enzymes.

This/these accessory or additional enzyme(s) may come both from the host cell and other microorganisms capable of secreting cellulolytic enzymes which have the aforementioned activities, for example, by means of a microorganism which belongs to the *Aspergillus* genus, such as *Aspergillus aculeatus, Aspergillus awamori, Aspergillus fumigatus, Aspergillus foetidus, Aspergillus japonicus, Aspergillus nidulans, Aspergillus niger,* or *Aspergillus oryzae; Fusarium*, such as *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum,*

*Fusarium pseudograminearum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Gibberella,* such as *Gibberella zeae; Humicola,* such as *Humicola insolens* or *Humicola lanuginosa; Trichoderma,* such as *Trichoderma harzianum, Trichoderma Trichoderma longibrachiatum, Trichoderma reesei,* or *Trichoderma viride;* or *Myceliophthora,* such as *Myceliophthora thermophila.*

Therefore, in a more preferred embodiment, the cocktail of the invention further comprises other accessory or additional cellulolytic enzymes as described in the previous paragraphs, which may be produced naturally or in recombinant manner.

In a more preferred embodiment, the cocktail of the invention is an enzymatic mixture produced from the host cell of the invention. In an even more preferred embodiment, the cocktail of the invention is an enzymatic mixture produced by means of the host cell of the invention, preferably *M. thermophila*, which has a lower expression and/or secretion of homologous non-contributory cellulolytic enzymes in relation to a host cell, preferably parental or wild-type *M. thermophila*, which has a normal expression and/or secretion of all cellulolytic enzymes.

The cocktail of the invention may be prepared according to the methods known in the state of the art and may be in liquid form or a dry composition. The enzymes that are going to be included in the cocktail may be established according to the methods known in the state of the art.

As previously indicated, the host cell of the invention is capable of secreting contributory enzymes into the medium together with other additional cellulolytic enzymes produced naturally or in recombinant manner, in this way being useful for the optimisation of the biomass hydrolysis stage in fermentable sugars.

Therefore, another aspect described in the invention relates to the use of the host cell of the invention or of the cocktail of the invention, for biomass degradation.

The host cell or the cocktail of the present invention may be used to produce, from biomass, preferably plant biomass, monosaccharides, disaccharides and polysaccharides as chemical raw materials or from fermentation for the production of ethanol, plastics or other products or intermediate products.

The host cell of the present invention may be used as a source of polypeptides which have cellulase activity, using said polypeptides in biomass degradation or hydrolysis and fermentation processes.

The biomass degradation or hydrolysis, preferably plant biomass, to fermentable sugars, process also known as "saccharification", by means of the host cell of the invention or of the cocktail of the invention, may be followed by a fermentation process wherein the fermentable sugars produced are used with the aim of finally producing a bioproduct such as bioethanol.

In this way, another preferred embodiment of this aspect of the invention relates to the use of the host cell of the invention or of the cocktail of the invention, for biomass degradation in a bioproduct production process.

The term "bioproduct" or "biobased products" relates to high value-added products which may be obtained by chemical transformation of the sugars or by fermentation of said sugars with different microorganisms. Without aiming to be limitative, a list of possible fermentative microorganisms is as follows: *Bacillus* the rmoglucosidaisus, *Clostridium butyricum, Corynebacterium glutamicum, Enterobacter aerogenes, Escherichia coli, Geobacillus thermoglucosidasius, Klebsiella oxytoca, Lactobacillus* sp. *Leunoscoc mesenteroides, Thermoanaerobacter* BG1L1, *Thermoanaerobacter ethanolicus, Thermoanaerobacter mathranii, Thermoanaerobacter thermosaccharolyticum, Zymobacter palmae, Zymomonas mobilis Candida arabinofermentans, Candida boidinii, Candida diddensis, Candida fermentans, Chrysosporium lucknowense, Candida pastoris, Candida shehatae, Candida sonorensis, Candida tropicalis, Hansenula anomala, Hansenula polymorpha, Kluyveromyces fragilis, Kluyveromyces marxianus, Pichia pastoris, Pichia stipitis, Saccharomyces cerevisiae, Saccharomyces bulderi, Saccharomyces bametti, Saccharomyces exiguus, Saccharomyces diastaticus, Saccharomyces uvarum* or *Schizosaccharomyces pombe* or mixtures thereof. These and other microorganisms may be provided by fermentation of different sugars, bioproducts among which it is possible to cite, in non-limitative manner, the following: alcohols such as ethanol, methanol, butanol, hexanol, octanol, decanol, dodecanol, 1,3-butanediol(1,3-diol), 1-alcohol; organic acids such as citric acid, acetic acid, itaconic acid, lactic acid, glutamic acid, succinic acid, beta-ketoacid, beta-ketoalcohol, beta-hydroxy acid; ketones such as acetone; gases such as hydrogen or carbon dioxide; hydrocarbons such as alkanes, alkenes or alkynes; nitrogenated substances such as amines, amide, nitro compounds or nitriles; halides, amino acids such as glutamic acid; antibiotics such as penicillin or tetracyclines; vitamin such as riboflavin, vitamin B12 or betacarotene; fatty acids such as dodecanoic acid, trans-$\Delta 2$ fatty acids or palmitic acid; and other products such as ethylene, glycerol, 1,3-propane-diol, betalactan, cephalosporins, trans fatty acids or furan.

Ethanol may be produced by means of the enzymatic degradation of the biomass and the conversion of the saccharides released in ethanol. This type of ethanol is often called bioethanol. It can be used as a fuel additive or extensor in mixtures of at least 1% up to 100% (a fuel replacement).

In a more preferred embodiment, the bioproduct is biofuel. The term "biofuel", as used here, relates to a hydrocarbon, or to one of its mixtures, which may be used as fuel and is produced using fermentable biomass as starting material. Examples of biofuels include, but are not limited to, ethanol or bioethanol and biodiesel. In a more preferred embodiment, the biofuel is bioethanol.

The term "bioethanol" relates to an alcohol prepared by means of fermentation, often from fermentable biomass such as carbohydrates produced in sugar or starch crops such as corn or sugarcane.

Another aspect of the present invention relates to a method to produce fermentable sugars, here called "first method of the invention" comprising:
  a) Incubating biomass, preferably pre-treated biomass, with the host cell of the invention, or with the cocktail of the invention, and
  b) Recovering the fermentable sugars produced after the incubation of stage (a).

Frequently, a biomass pre-treatment method is required to increase the access of enzymes to their substrates and the consequent efficient hydrolysis. The pre-treatment uses various techniques, which include, but are not limited to, chemical and/or mechanical treatments, such as, for example, explosion of the fibre with ammonium, treatment with diluted acid and steam explosion at high temperatures to alter the structure of the cellulosic biomass and make the cellulose more accessible. The use of the host cell of the invention or the cocktail of the invention in the methods of the present invention is advantageous since high temperatures are not required in the biomass pre-treatment process.

The term "fermentable sugar" as used here, relates to simple sugars, such as glucose, xylose, arabinose, galactose, mannose, rhamnose, saccharose or fructose, among others.

Another aspect described in the present invention relates to a method to produce a bioproduct from biomass, hereinafter called "second method of the invention", comprising:
a) Incubating biomass, preferably pre-treated biomass, with the host cell of the invention or with the cocktail of the invention,
b) Fermenting the fermentable sugars produced after incubation stage (a) with at least one fermenting microorganism, and
c) Recovering the bioproduct produced after the fermentation of stage (b).

Before (i.e. in stage (a)) and/or simultaneously with the fermentation of stage (b), the biomass, preferably pre-treated biomass, is hydrolysed to degrade the cellulose and hemicellulose in sugars and/or oligosaccharides. The solid content during hydrolysis may be, but without limitation, between 5-40% of the total weight, preferably between 10-40% of the total weight, more preferably between 15-25% of the total weight. Hydrolysis is performed as a process wherein the biomass, preferably pre-treated biomass, is incubated with the host cell of the invention or with the cocktail of the invention which contains cellulolytic enzymes and thus form the hydrolysis solutions. The suitable process time, the temperature and the pH conditions may be easily determined by a person skilled in the art. Preferably, said hydrolysis is performed at a temperature between 25° C. and 60° C., preferably between 40° C. and 60° C., specifically around 50° C. The process is performed preferably at a pH in the range of 3-8, preferably pH 4-6, especially around pH 5. Preferably, the hydrolysis is performed in a time between 12 and 144 hours, preferably between 16 and 120 hours, more preferably between 24 and 96 hours, even more preferably between 32 and 72 hours.

The hydrolysis (stage (a)) and the fermentation (stage (b)) may be simultaneously (SSF process) or sequentially (SHF process) performed. According to the invention, the hydrolysed and, preferably pre-treated biomass, is fermented by at least one fermenting microorganism capable of fermenting fermentable sugars, such as glucose, xylose, mannose and galactose, directly or indirectly, in the desired fermentation product. The fermentation is carried out preferably in a time between 8 and 96 hours, preferably between 12 and 72, more preferably between 24 and 48 hours. In another preferred embodiment, the fermentation is performed at a temperature between 20° C. and 40° C., preferably from 26° C. to 34° C., in particular around 32° C. In another preferred embodiment, the pH is of 3 to 6 units, preferably from 4 to 5. For ethanol fermentation, a yield of the *Saccharomyces cerevisiae* species is preferred, both wild-type and genetically modified. The strains resistant to high ethanol levels are preferred, up to, for example, 5 or 7% vol. of ethanol or more, such as 100% vol. of ethanol.

The term "fermenter or fermentation" as used here, relates to a biological transformation process produced by the activity of some microorganisms wherein sugars such as glucose, fructose, and saccharose turn into ethanol. The microorganisms used in this way are fermenting microorganisms, that have fermentation capacity, preferably *S. cerevisiae*.

The term "recovery" as used here, relates to the collection of fermentable sugars produced after the incubation of stage (a) of the first method of the invention or of the bioproduct produced after the fermentation of stage (b) of the second method of the invention. The recovery can be performed by any method known in the state of the art, including mechanical or manual.

In a preferred embodiment of the second method of the invention, the bioproduct is biofuel, more preferably bioethanol.

Throughout the description and the claims, the word "comprises" and its variants are not intended to exclude other technical characteristics, additives, components or steps. For persons skilled in the art, other objects, advantages and characteristics of the invention will be inferred in part from the description and in part from the practice of the invention. The following figures and examples are provided by way of illustration, and are not intended to limit the present invention.

EXAMPLES

Figure 1A:
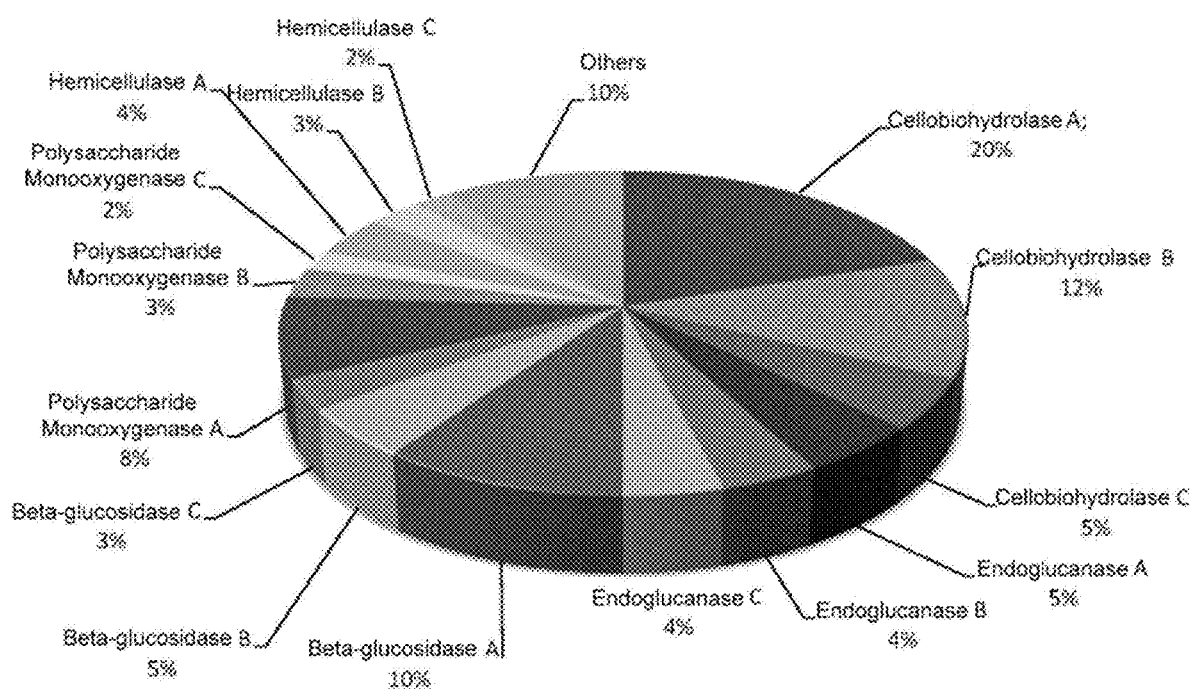
FIG. 1. (A). Representation of the composition and concentration (expressed in the form of relative percentage) of cellulase enzymes included in an enzymatic cocktail that could be produced from a non-genetically modified parental host cell. (B). Representation of the composition and concentration (expressed in the form of relative percentage) of cellulase enzymes included in an enzymatic cocktail that could be produced from a modified host cell as described in the present invention. As observed in FIG. 1B, said enzymatic cocktail shows a lower enzymatic diversity and a greater representation of contributory enzymes, more efficient in the industrial conditions wherein they will be used, to the detriment of the diversity thereof.
Figure 1B:
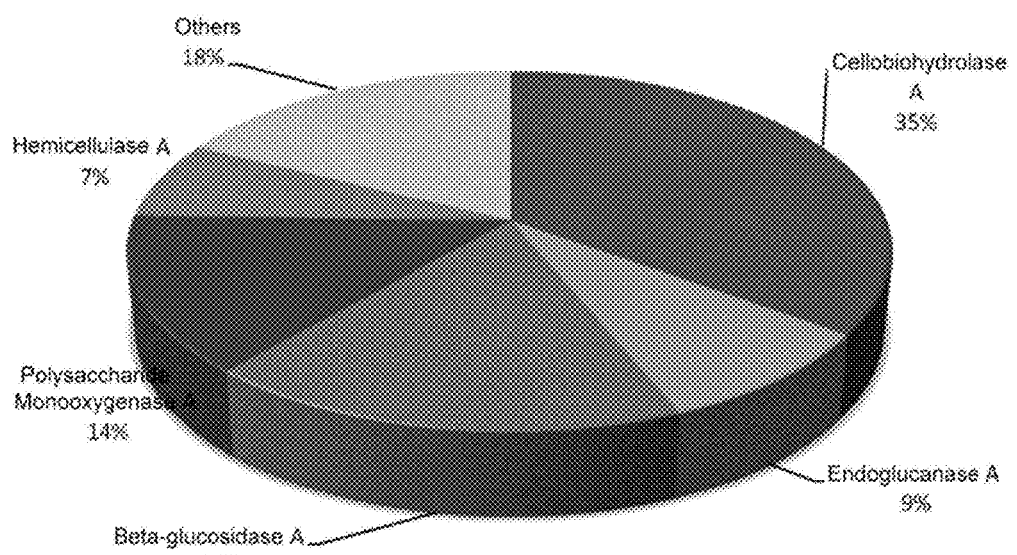

The invention shall be illustrated below, by means of assays that reveal the effectiveness of the object of the invention.

Example 1. Construction of a Plasmid Capable of Deleting the Eg6 Gene. Transformation of the *M. thermophila* Strain with Said Plasmid for the Production of the ΔEg6 Strain The eg6 gene (SEQ ID NO: 1) of *M. thermophila* C1 was the candidate gene to be deleted given its improvement potential in the enzymatic composition lacking this activity. To do this, a plasmid was constructed which enabled deleting the eg6 gene in *M. thermophila* C1. Said plasmid has fragments upstream and downstream of the eg6 gene so that by means of homologous recombination with the genome of *M. thermophila* C1, the eg6 gene is replaced by the selection marker cloned between both fragments.

The downstream fragment of the eg6 gene was amplified from genomic DNA of *M. thermophila* C1 as target (obtained using the DNeasy Plant Mini Kit from Qiagen) with the polymerase DNA iProof High-Fidelity (BioRad) using oligonucleotides 1 (direct primer) (ACCGAGCTCGT-AGCACTCGCTGTGTATCCTC) (SEQ ID NO: 7) and 2 (inverse primer) (CCTGGATCCCTTATACCCAGGACAT-TCACAGTTC) (SEQ ID NO: 8). These oligos include recognition sequences for the restriction enzymes SacI and BamHI. In the same way, the downstream fragment of the eg6 gene was amplified with oligonucleotides 3 (direct primer) (ACCGAATTCATCAAATGGATAGGTCGG-TAATG) (SEQ ID NO: 9) and 4 (inverse primer) (CACCTCGAGCAAGGAAGTCGAGTACGAGTCC) (SEQ ID NO: 10). These oligonucleotides include recognition sequences of the restriction enzymes EcoRI and XhoI. The amplification conditions for both fragments are one cycle at 95° C. during 2 minutes and 30 cycles of 98° C. during 10 seconds, 55° C. during 20 seconds, 72° C. during 90 seconds and 72° C. during 10 minutes.

Figure 2A:
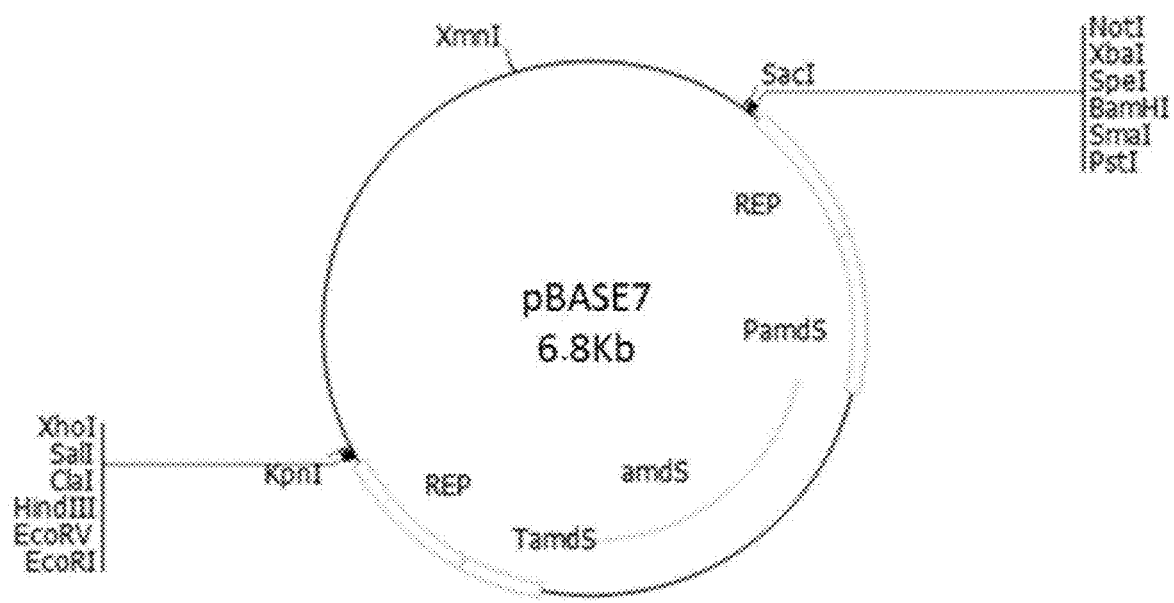
FIG. 2. (A) Diagram of the pBASE7 vector. Base plasmid that enables cloning the flanking ends of the gene that it is intended to delete. As selection marker it includes the amdS gene, which confers resistance to acetamide. The selection marker includes its promoter region ($P_{amdS}$) and terminator region ($T_{amdS}$). On both sides of the amdS gene there are two REP (repeated) regions which allow, once the vector is integrated in the genome and by means of homologous recombination between them, the elimination of the amdS selection marker. (B) Diagram of the pBASE7-eg6 plasmid used to delete the eg6 gene. The upstream regions (region 5') and downstream regions (region 3') of the eg6 gene have cloned in the pBASE7 vector. This plasmid, once linearised, shall be used to delete the eg6 gene.
Figure 2B:
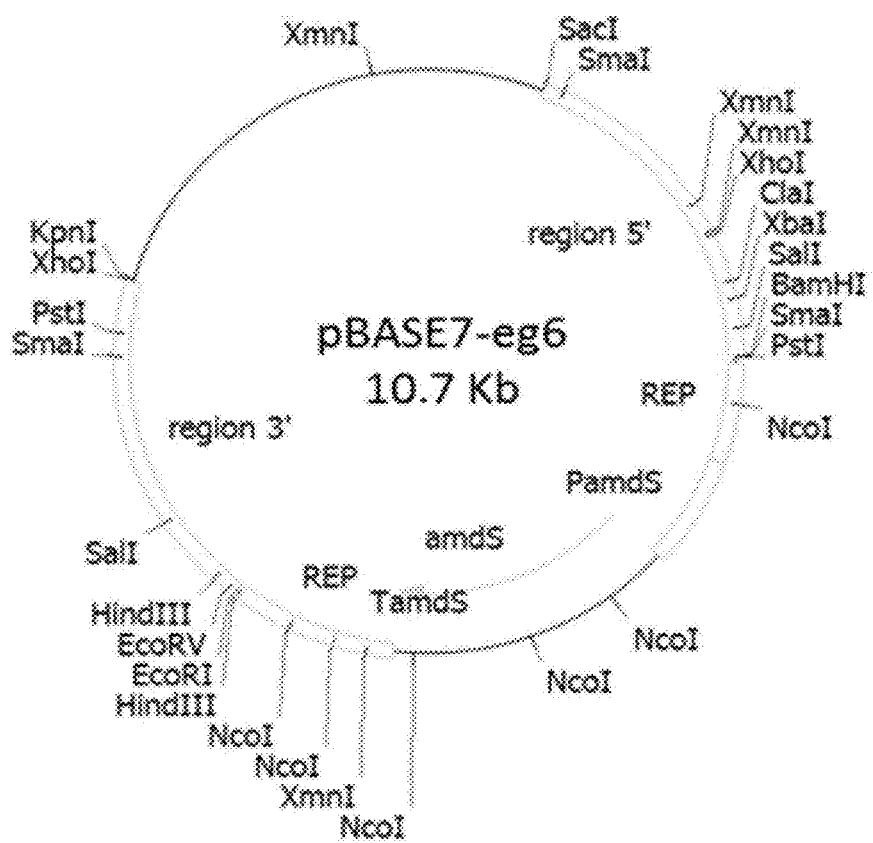

After amplifying the upstream and downstream fragments of the eg6 gene, of sizes corresponding to 2005 pb and 2018 pb respectively, they were cloned in the pBASE7 vector (FIG. 2A). This vector contains the amdS gene as selection marker, which gives the capacity of using acetamide as nitrogen source. Firstly, the amplified fragment corresponding to end 3' of the gene (situated downstream thereof) was digested with the restriction enzymes EcoRI and XhoI and it was cloned in the pBASE7 vector previously digested with the same restriction enzymes. The ligation mixture was transformed in electrocompetent cells of *Escherichia coli* XL1Blue MRF following the protocol provided by the manufacturer (Stratagene). After this plasmid was produced, the end situated upstream of the eg6 gene was continued to be cloned. To do this, the corresponding fragment was digested with the restriction enzymes SacI and KpnI and it was cloned in the plasmid where the downstream end had previously been cloned. The ligation mixture was transformed in electrocompetent cells of *Escherichia coli* XL1Blue MRF following the protocol provided by the manufacturer (Stratagene). The plasmid produced (pBASE7-eg6) is shown in FIG. 2B.

The plasmid DNA to delete the eg6 gene was linearised by means of digestion with the restriction enzymes SacI and BamHI and it was used to transform host cells of the strain *M. thermophila* C1 (Verdoes et al., 2007, Ind. Biotechnol., 3 (1)). This DNA was introduced in the host strain using a protoplast transformation method (U.S. Pat. No. 7,399, 627B2). The transformers were inoculated in agar dishes containing 0.6 g/L of acetamide (Merck). After 5 days of incubation at 35° C., the resulting transformers (which express the amdS gene and are therefore capable of growing in the presence of acetamide as only source of nitrogen) were analysed. The transformers obtained were genetically analysed to verify if the eg6 gene had been replaced by the selection marker. To do this, genomic DNA was obtained from the transformers produced (produced using the DNeasy Plant Mini Kit from Qiagen) with the polymerase DNA iProof High-Fidelity (BioRad) using oligonucleotides 5 (direct primer) (GGCTCGAGATCTACAAGACTG) (SEQ ID NO: 11) and 6 (inverse primer) (GTAGTTGGA-CACGTTGGTGA) (SEQ ID NO: 12) to amplify an internal fragment of eg6 of 350 pb. The amplification conditions for both fragments are one cycle at 95° C. during 2 minutes and 30 cycles of 95° C. during 30 seconds, 55° C. during 30 seconds, 72° C. during 30 seconds and 72° C. during 10 minutes.

Figure 3:
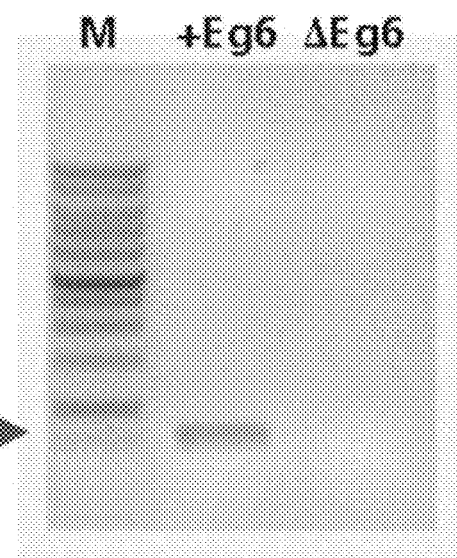
FIG. 3. Genetic verification of deletion of the eg6 gene. Amplification by means of PCR of an internal fragment of 350 pb of the eg6 gene. This amplification is negative in the case of Δeg6, which is the strain wherein the eg6 gene has been deleted.

In this example it identifies those host cells that have been transformed and which do not express the eg6 gene (negative amplification) compared with those host cells that express said gene (positive amplification). In this way, strain *M. thermophila* C1 Δeg6 was identified. FIG. 3 shows the genetic test after the amplification of an internal fragment of eg6 of 350 pb. This amplification is negative in the case of strain Δeg6.

Example 2. Evaluation of Host Strains of *M. thermophila* which Lack the Non-Contributory Cellulase Eg6 (ΔEg6) Compared with the Parental Strains that do Contain it (+Eg6)

The release of fermentable sugars from the *M. thermophila* C1 Δeg6 strain was compared with its parental strain+ Eg6. Pre-treated corn biomass ("pre-treated corn stover", or PCS) was used as substrate for the enzymatic hydrolysis. The pre-treatment was performed by means of a steam explosion system (Nguyen et al., 1998, Appl. Biochem. Biotechnol. 70-72), and its composition analysis was performed in accordance with the methods described by NREL in "Standard Biomass Analytic Procedures" (http://www.n-rel.gov/biomass/analytic_procedures.htmL). With the object of its use in hydrolysis, the biomass was previously neutralised adjusting it to a pH of 5.5. For the enzymatic hydrolysis process, 100 ml ISO bottles were used with 20 g of the 20% reaction mixture (w/w) of total solids and supplemented with 12 mg protein per g of glucan of the cocktail from strains Δeg6 and +Eg6, respectively. The bottles with the mixture were incubated during 72 h at 50° C. with 150 rpm stirring in a 25 mm-diameter orbital incubator (Infors HT). Once the process was performed, the glucose content in the resulting samples of the slurry was analysed by HPLC (Agilent Technologies, 1200 Series) using a refraction index detector (RID) and an Aminex column (HPX-87 H).

Figure 4:
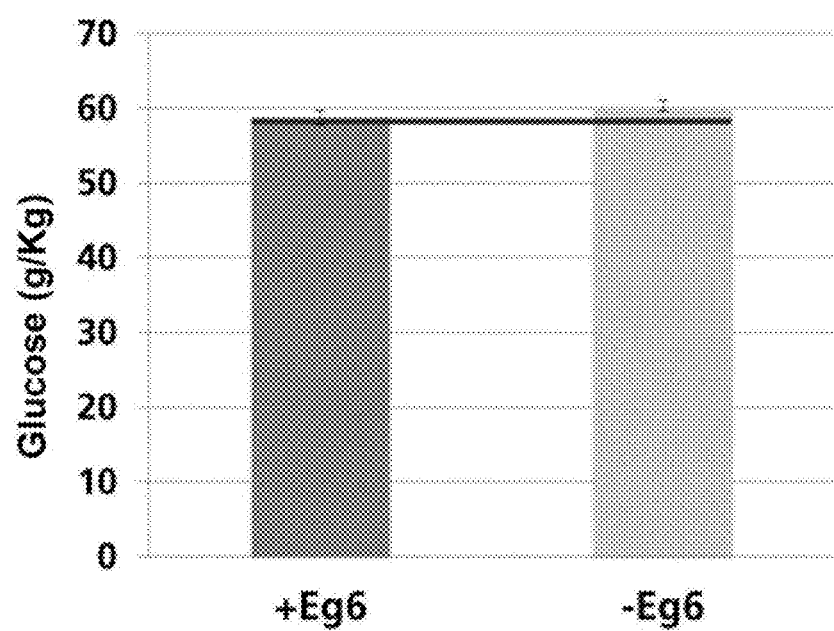
FIG. 4. Analysis of the release of glucose from ground biomass subjected to a cellulolytic enzymatic composition produced from a strain of *M. thermophila* which does not express the eg6 gene with respect to the parental strain of *M. thermophila*.

The results obtained are shown in FIG. 4, where it can be observed that deletion of the non-contributory endoglucanase Eg6 causes an increase in saccharification capacity, i.e. glucose production with respect to the control that does express endoglucanase Eg6.

Figure 5:
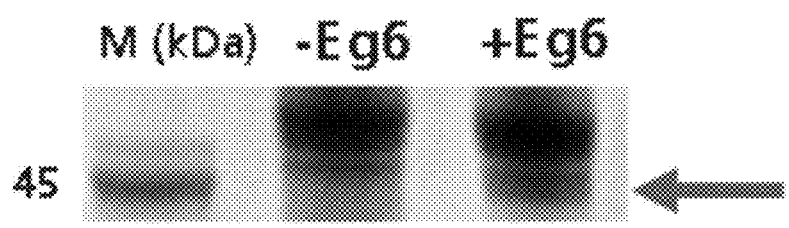
FIG. 5. Photograph of polyacrylamide gel electrophoresis (SDS-PAGE 7.5%) showing the cellulases present in two enzymatic compositions, one contains the endoglucanase 6 (+Eg6) enzyme, which has been produced from an unmodified control strain of *M. thermophila*, and another that lacks said enzyme (−Eg6). Lane 1: Molecular weight marker; Lane 2: enzymatic composition without Eg6; Lane 3: enzymatic composition with Eg6. The arrow indicates the protein band that corresponds to the endoglucanase 6 enzyme.

FIG. 5 shows the acrylamide gel electrophoresis in denaturing conditions (SDS-PAGE) of the enzymatic compositions with and without Eg6.

Example 3. Evaluation of *M. thermophila* Strains that Lack the Non-Contributory Enzyme PMO-09768 (ΔPMO-09768) Compared with the Parental Strains that do Contain it In the same way as has been described for the production of a deleted strain for the eg6 gene (see Example 1), a strain was produced which had deletion of the PMO-09768 gene and which was called ΔPMO-09768. The release of fermentable sugars from the *M. thermophila* C1 ΔPMO-09768 strain was compared with its parental strain. Pre-treated corn biomass ("pre-treated corn stover", or PCS) was used as substrate for the enzymatic hydrolysis. The pre-treatment was performed by means of a steam explosion system (Nguyen et al., 1998, Appl. Biochem. Biotechnol. 70-72), and its composition analysis was performed in accordance with the methods described by NREL in "Standard Biomass Analytic Procedures" (http://www.nrel.gov/biomass/analytic_procedures.htmL). With the object of its use in hydrolysis, the biomass was previously neutralised adjusting it to a pH of 5.5. For the enzymatic hydrolysis process, 100 ml ISO bottles were used with 20 g of the 20% reaction mixture (w/w) of total solids and supplemented with 12 mg protein per g of glucan of the cocktail from the strains in question. The bottles with the mixture were incubated during 72 h at 50° C. with 150 rpm stirring in a 25 mm-diameter orbital incubator (Infors HT). Once the process was performed, the glucose content in the resulting samples of the slurry was analysed by HPLC (Agilent Technologies, 1200 Series) using a refraction index detector (RID) and an Aminex column (HPX-87 H).

Figure 6:
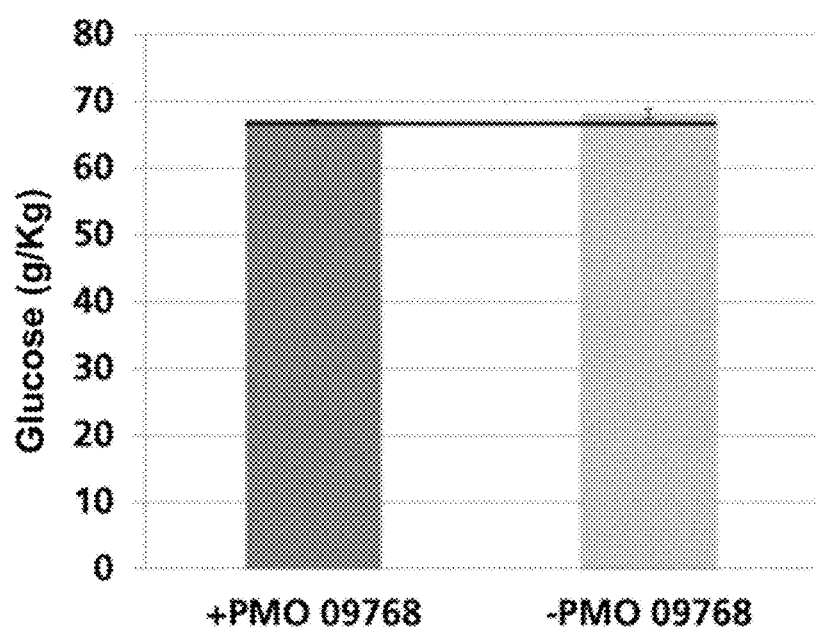
FIG. 6. Analysis of the release of glucose from ground biomass subjected to a cellulolytic enzymatic composition produced from a strain of *M. thermophila* which does not express the polysaccharide monooxygenase 09768 gene with respect to the parental strain of *M. thermophila*.
Figure 7:
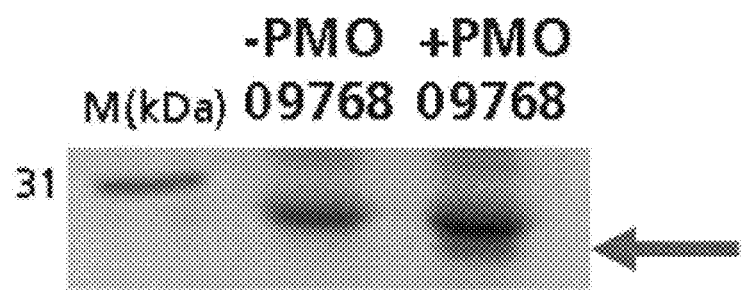
FIG. 7. Photograph of polyacrylamide gel electrophoresis (SDS-PAGE 7.5%) showing the cellulases present in two enzymatic compositions, one comprising the polysaccharide mono oxygenase enzyme (+PMO 09768), which has been produced from an unmodified control strain of *M. thermophila*, and another that lacks said enzyme (−PMO 09768). Lane 1: Molecular weight marker; Lane 2: enzymatic composition without PMO 09768; Lane 3: enzymatic composition with PMO 09768. The arrow indicates the protein band that corresponds to the PMO 09768 enzyme.

The results obtained are shown in FIG. 6, where it is possible to observe that deletion of the non-contributory PMO 09768 causes an increase in saccharification capacity with respect to the control, i.e. in the production of glucose by the cellulase mixture. FIG. 7 shows the acrylamide gel electrophoresis in denaturing conditions (SDS-PAGE) of the enzymatic compositions with and without PMO-09768.

Example 4. Evaluation of the Effect of Deletion of the Eg6 Gene (Non-Contributory Endoglucanase) in Different Strains of *M. thermophila*

The gene which codes for the non-contributory endoglucanase Eg6 (SEQ ID NO: 1) was deleted in several strains of *M. thermophila* with the aim of demonstrating the positive effect that said deletion has on the enzymatic composition produced by said strains. A method similar to that described in Example 1 was used for the construction of the strains.

Two different strains were produced which had a deletion in the eg6 gene with respect to the parental strains as described in Example 1.

Figure 8:
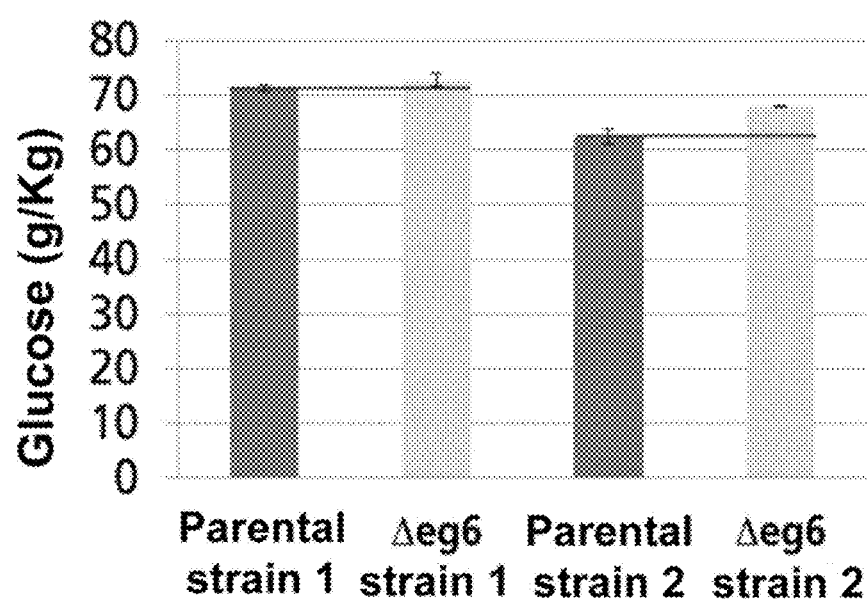
FIG. 8. Analysis of the release of glucose from ground biomass subjected to a cellulolytic enzymatic composition produced from strains of *M. thermophila* which do not express the gene which codes for endoglucanase 6 with respect to the respective strains of parental *M. thermophila* that do express said gene.

As shown in FIG. 8, the enzymatic composition produced by both strains of *M. thermophila* which lack the non-contributory endoglucanase Eg6 is capable of releasing greater glucose concentration than the enzymatic compositions secreted by the parental strains containing the Eg6 enzyme.

The invention claimed is:

1. A genetically engineered host cell modified by homologous recombination to delete a gene of SEQ ID NO: 1 encoding a cellulolytic enzyme comprising SEQ ID NO: 2 in the said host cell, wherein said genetically engineered host cell lacks cellulolytic enzyme activity of the polypeptide of SEQ ID NO: 2.

2. The host cell according to claim 1, wherein the host cell is *Myceliophthora thermophila*.

3. A method of producing fermentable sugars comprising:
   (a) Incubating biomass with a genetically engineered host cell modified by homologous recombination to delete a gene of SEQ ID NO: 1 encoding a cellulolytic enzyme comprising SEQ ID NO: 2 in the said host cell, wherein said genetically engineered host cell lacks cellulolytic enzyme activity of the polypeptide of SEQ ID NO: 2, and
   (b) Recovering the fermentable sugars produced after the incubation of step (a).

4. A method of producing a bio product from biomass comprising:
   (a) Incubating biomass with a genetically engineered host cell modified by homologous recombination to delete a gene of SEQ ID NO: 1 encoding a cellulolytic enzyme comprising SEQ ID NO: 2 in the said host cell, wherein said genetically engineered host cell lacks cellulolytic enzyme activity of the polypeptide of SEQ ID NO: 2,
   (b) Fermenting the fermentable sugars produced after the incubation of step (a) with at least one fermenter microorganism, and
   (c) Recovering the bio product produced after the fermentation in step (b).

5. The method according to claim 4, wherein the bio product is biofuel.

6. The method according to claim 5, wherein the biofuel is bioethanol.

* * * * *

SEQUENCE LISTING

```
<160> NUMBER OF SEQ ID NOS: 12

<210> SEQ ID NO 1
<211> LENGTH: 1223
<212> TYPE: DNA
<213> ORGANISM: Myceliophthora thermophila

<400> SEQUENCE: 1
atgcgcgtct ctagtttggt cgcggccctt gctaccggtg gtcttgtcgc cgccacgcct      60
aagcccaagg ggtcgtcgcc ccctggggcc gtggacgcga accctttcaa gggcaagacg     120
cagttcgtca acccggcatg ggcggccaag ctggaacaga ccaaaaaggc gttcctggcc     180
aggaacgaca ccgtcaatgc cgccaagacg gagaaggtcc agcagaccag ctcgttcgtc     240
tgggtctcga ggatcgccga gctctccaac atcgacgacg ccatcgcggc tgcccgcaag     300
gcgcagaaga agacgggcag gaggcagatc gtcggcctgg tgctctacaa ccttccggac     360
cgcgactgca gcgcgggcga gagcgcgggc gagctcagca gcgacaagaa cgggctcgag     420
atctacaaga ctgagttcgt caagcccttc gccgacaagg tggcggccgc aaaggacctc     480
gacttcgcca tcgtcctgga gcccgactcg ctggccaacc tggtcaccaa cctgggcatc     540
gagttctgcg ccaacgccgc cccgtctac cgcgagggca tcgcctatgc catctccagc     600
```

```
cttcagcagc caaacgtgca cttgtacatc gatgctgccc acggcggctg gctcggctgg      660
gacgacaacc tgccgctggc cgccaaggag tttgccgagg tggtcaagct tgccggcgag      720
ggcaagaaga tccgcggctt cgtcaccaac gtgtccaact acaacccctt ccacgccgtc      780
gtgcgcgaga actttaccga gtggagcaac tcgtgggacg agtctcacta cgcctcctcg      840
ctcacaccgt tcctcgagaa agaggggctg ccggcacgct tcatcgtcga ccagggtcgc      900
gttgccctcc cgggagcccg caaggagtgg tgagtttcga ccagattgac cctcgaccca      960
tgcgaccgag attgctgacg attgaattgc gtgtcccgtc ccccaggggt gaatggtgca     1020
acgtggcacc cgccggattt ggccccgcgc ccacgaccag ggtcaacaac accgtcgtcg     1080
atgctctcgt ctgggtcaag cctggcggcg agagcgacgg cgagtgtggc ttggctggcg     1140 ccccaaggc cggccagtgg ttcgacgagt acgcccagat gctggtcgag aatgcccacc      1200
cgtctgtcgt ccacaagtgg tag                                             1223
```

<210> SEQ ID NO 2
<211> LENGTH: 381
<212> TYPE: PRT
<213> ORGANISM: Myceliophthora thermophila

<400> SEQUENCE: 2

```
Met Arg Val Ser Ser Leu Val Ala Ala Leu Ala Thr Gly Gly Leu Val
1               5                   10                  15

Ala Ala Thr Pro Lys Pro Lys Gly Ser Ser Pro Gly Ala Val Asp
            20                  25                  30

Ala Asn Pro Phe Lys Gly Lys Thr Gln Phe Val Asn Pro Ala Trp Ala
            35                  40                  45

Ala Lys Leu Glu Gln Thr Lys Lys Ala Phe Leu Ala Arg Asn Asp Thr
50                  55                  60

Val Asn Ala Ala Lys Thr Glu Lys Val Gln Gln Thr Ser Ser Phe Val
65                  70                  75                  80

Trp Val Ser Arg Ile Ala Glu Leu Ser Asn Ile Asp Asp Ala Ile Ala
                85                  90                  95

Ala Ala Arg Lys Ala Gln Lys Lys Thr Gly Arg Arg Gln Ile Val Gly
            100                 105                 110

Leu Val Leu Tyr Asn Leu Pro Asp Arg Asp Cys Ser Ala Gly Glu Ser
            115                 120                 125

Ala Gly Glu Leu Ser Ser Asp Lys Asn Gly Leu Glu Ile Tyr Lys Thr
130                 135                 140

Glu Phe Val Lys Pro Phe Ala Asp Lys Val Ala Ala Lys Asp Leu
145                 150                 155                 160

Asp Phe Ala Ile Val Leu Glu Pro Asp Ser Leu Ala Asn Leu Val Thr
                165                 170                 175

Asn Leu Gly Ile Glu Phe Cys Ala Asn Ala Ala Pro Val Tyr Arg Glu
            180                 185                 190

Gly Ile Ala Tyr Ala Ile Ser Ser Leu Gln Gln Pro Asn Val His Leu
            195                 200                 205

Tyr Ile Asp Ala Ala His Gly Gly Trp Leu Gly Trp Asp Asp Asn Leu
210                 215                 220

Pro Leu Ala Ala Lys Glu Phe Ala Glu Val Val Lys Leu Ala Gly Glu
225                 230                 235                 240

Gly Lys Lys Ile Arg Gly Phe Val Thr Asn Val Ser Asn Tyr Asn Pro
                245                 250                 255
```

```
Phe His Ala Val Val Arg Glu Asn Phe Thr Glu Trp Ser Asn Ser Trp
            260                 265                 270

Asp Glu Ser His Tyr Ala Ser Ser Leu Thr Pro Phe Leu Glu Lys Glu
        275                 280                 285

Gly Leu Pro Ala Arg Phe Ile Val Asp Gln Gly Arg Val Ala Leu Pro
    290                 295                 300

Gly Ala Arg Lys Glu Trp Gly Glu Trp Cys Asn Val Ala Pro Ala Gly
305                 310                 315                 320

Phe Gly Pro Ala Pro Thr Thr Arg Val Asn Asn Thr Val Val Asp Ala
                325                 330                 335

Leu Val Trp Val Lys Pro Gly Gly Glu Ser Asp Gly Glu Cys Gly Leu
            340                 345                 350

Ala Gly Ala Pro Lys Ala Gly Gln Trp Phe Asp Glu Tyr Ala Gln Met
        355                 360                 365

Leu Val Glu Asn Ala His Pro Ser Val Val His Lys Trp
    370                 375                 380

<210> SEQ ID NO 3
<211> LENGTH: 749
<212> TYPE: DNA
<213> ORGANISM: Myceliophthora thermophila

<400> SEQUENCE: 3
atgctgacaa caaccttcgc cctcctgacg gccgctctcg gcgtcagcgc ccattatacc      60
ctccccaggg tcgggaccgg ttccgactgg cagcacgtgc ggcgggctga caactggcaa     120
aacaacggct tcgtcggcga cgtcaactcg agcagatcag gtgcttccag gcgacccct     180 gccggcgccc aagacgtcta cactgttcag gcgggatcga ccgtgaccta ccacgccaac     240
cccagtatct accaccccgg ccccatgcag ttctacctgg cccgcgttcc ggacggacag     300
gacgtcaagt cgtggaccgg cgagggtgcc gtgtggttca aggtgtacga ggagcagcct     360
caatttggcg cccagctgac ctggcctagc aacggtgcgt tgatcatttt ccttcttctt     420
ccttctttct tccgttgcat atgctaactg ttctcttgct tgcaggcaag agctcgttcg     480
aggttcctat ccccagctgc attcgggcgg gcaactacct cctccgcgct gagcacatcg     540
ccctgcacgt tgcccaaagc cagggcggcg cccagttcta catctcgtgc gcccagctcc     600
aggtcactgg tggcggcagc accgagcctt ctcagaaggt ttccttcccg ggtgcctaca     660
agtccaccga ccccggcatt cttatcaaca tcaactaccc cgtccctacc tcgtaccaga     720
atccgggtcc ggctgtcttc cgttgctaa                                       749

<210> SEQ ID NO 4
<211> LENGTH: 225
<212> TYPE: PRT
<213> ORGANISM: Myceliophthora thermophila

<400> SEQUENCE: 4

Met Leu Thr Thr Thr Phe Ala Leu Leu Thr Ala Ala Leu Gly Val Ser
1               5                   10                  15

Ala His Tyr Thr Leu Pro Arg Val Gly Thr Gly Ser Asp Trp Gln His
            20                  25                  30

Val Arg Arg Ala Asp Asn Trp Gln Asn Gly Phe Val Gly Asp Val
        35                  40                  45

Asn Ser Glu Gln Ile Arg Cys Phe Gln Ala Thr Pro Ala Gly Ala Gln
    50                  55                  60

Asp Val Tyr Thr Val Gln Ala Gly Ser Thr Val Thr Tyr His Ala Asn
```

```
                65                  70                  75                  80
Pro Ser Ile Tyr His Pro Gly Pro Met Gln Phe Tyr Leu Ala Arg Val
                    85                  90                  95
Pro Asp Gly Gln Asp Val Lys Ser Trp Thr Gly Glu Gly Ala Val Trp
                100                 105                 110
Phe Lys Val Tyr Glu Glu Gln Pro Gln Phe Gly Ala Gln Leu Thr Trp
                115                 120                 125
Pro Ser Asn Gly Lys Ser Ser Phe Glu Val Pro Ile Pro Ser Cys Ile
            130                 135                 140
Arg Ala Gly Asn Tyr Leu Leu Arg Ala Glu His Ile Ala Leu His Val
145                 150                 155                 160
Ala Gln Ser Gln Gly Gly Ala Gln Phe Tyr Ile Ser Cys Ala Gln Leu
                165                 170                 175
Gln Val Thr Gly Gly Gly Ser Thr Glu Pro Ser Gln Lys Val Ser Phe
            180                 185                 190
Pro Gly Ala Tyr Lys Ser Thr Asp Pro Gly Ile Leu Ile Asn Ile Asn
                195                 200                 205
Tyr Pro Val Pro Thr Ser Tyr Gln Asn Pro Gly Pro Ala Val Phe Arg
            210                 215                 220
Cys
225
```

<210> SEQ ID NO 5
<211> LENGTH: 3310
<212> TYPE: DNA
<213> ORGANISM: Myceliophthora thermophila
<220> FEATURE:
<221> NAME/KEY: promoter
<222> LOCATION: (1)..(740)
<220> FEATURE:
<221> NAME/KEY: terminator
<222> LOCATION: (2359)..(3310)

<400> SEQUENCE: 5

```
aggttttgtg cggtatggag ctaataatat tgaacggatc tctggtccgt cctaaatcgt      60
tgaaacgcta ggcccagaag gacctgctcg acttggcgaa cggagatttc caggacgaaa     120
gtcggaacat ctccatccgc ggccaacctg aacacttttg ttcgtttccg gaccatcgac     180
ccacgaaaac agtgcggttg ctggcacagt cagtactcac aatggcgatg gtccagcccg     240
ttcccgcccg atgcccactt gcagcgcaac tctccttcgt tcggcggccc ggcggtgtct     300
ggcctattag tacgattttg gataccggct tggtcgccgc cgcggttttt cttggccgat     360
acgggaatct cggtggtccc aactccacct gggcacgctc tggtgccaac atggaacttc     420
gggatgccgc tccgggcaca gtcaagcgct ttaaaatgcg accttactcc acaagaatcg     480
aggcgtaacc cggaattagg gacgcctgga cggcgcaacc cctggaccga agggcctcgc     540
taaccgggtt cctggagccg catgcgcggc tgcccgcttg cccgctcttg aggtgacact     600
tcttttcaac gagcgatggc cgggcaggaa aatgatgtat aagaagcgag ccgattccga     660
cggactcgac ctctctctcg cctcttgccc tgtgtccgcg agctaattac agcagtcctt     720
ctcgacttga aacgcccaa atgaagtcct ccatcctcgc cagcgtcttc gccacgggcg     780
ccgtggctca aagtggtccg tggcagcaat gtggtggcat cggatggcaa ggatcgaccg     840
actgtgtgtc gggctaccac tgcgtctacc agaacgattg gtacagccag tgcgtgcctg     900
gcgcggcgtc gacaacgctg cagacatcga ccacgtccag gcccaccgcc accagcaccg     960
ccccctccgt c gtccaccacc tcgcctagca agggcaagct gaagtggctc ggcagcaacg    1020
```

```
agtcgggcgc cgagttcggg gagggcaatt accccggcct ctggggcaag cacttcatct    1080
tcccgtcgac ttcggcgatt caggtacggc caataataat atattattat agcaggcagg    1140
agggagcagg agaagaaggg aggggcaggt ggcccacaat cggaagaaga ccgggaggca    1200
ctgaccgttg attcctttgt gtaatagacg ctcatcaatg atggatacaa catcttccgg    1260
atcgacttct cgatggagcg tctggtgccc aaccagttga cgtcgtcctt cgaccagggt    1320
tacctccgca acctgaccga ggtggtcaac ttcgtgacga acgcgggcaa gtacgccgtc    1380
ctggacccgc acaactacgg ccggtactac ggcaacatca tcacggacac gaacgcgttc    1440
cggaccttct ggaccaacct ggccaagcag ttcgcctcca actcgctcgt catcttcgac    1500
accaacaacg agtacaacac gatggaccag accctggtgc tcaacctcaa ccaggccgcc    1560
atcgacggca tccgggccgc cggcgcgacc tcgcagtaca tcttcgtcga gggcaacgcg    1620
tggagcgggg cctggagctg aacacgacc aacaccaaca tggccgccct gacggacccg    1680
cagaacaaga tcgtgtacga gatgcaccag tacctcgact cggacagctc gggcacccac    1740
gccgagtgcg tcagcagcac catcggcgcc cagcgcgtcg tcggagccac ccagtggctc    1800
cgcgccaacg gcaagctcgg cgtcctcggc gagttcgccg gcggcgccaa cgccgtctgc    1860
cagcaggccg tcaccggcct cctcgaccac ctccaggaca acagcgacgt ctggctgggt    1920
gccctctggt gggccgccgg tccctggtgg ggcgactaca tgtactcgtt cggtaagttt    1980
ctcccttgtt cttggtttcc cccccaaata agggagtcag gcaacatgcc caagatcggc    2040
tcggcttcgc ttcaaggcgt tcgttgtaca cactgaagag ttccaactcc caacctgttc    2100
gtgtcctccg atcagcttca acggggtga aggggaagg gatttgggag tgaggtggag    2160
gtcaaaagga ggggtattat ccccagacct ccacaaacgg ccctgagcca acagcctctg    2220
gggtcaaaat gggcgccaac catacggtca ttcactcagg acacctgcta acgcgcctct    2280 tttttttgt ttccagagcc tccttcgggc accggctatg tcaactacaa ctcgatcttg    2340
aagaagtact tgccgtaagg ggcgtgcagc aaggtcgagc gagcattatt cggggccatc    2400
tgcttgtgtc ggcaggcatc acgtcaaccc atcgaattgg acagcggaat gctccgagac    2460
gccctacact aagtctggtg atgatcccgg acgctgccgc gcccggatac catgatttca    2520
tgtacatatt ggttctttgc tttcttaccg gggggctct gcagcgttgc tgagcgattc    2580
gtttccaagt atatactttg tctggaattg aattttgggt gacattgacc caatcaacca    2640
gctcggcgtg ctcacctccc gttacccccc ctcttctccc cctgctcggc ttggctttcc    2700
tctccggtgt ggagcacggc cacggcggtc tcaatccata caggaagata agatcgatgg    2760
tttcctatgg tatacactac ttgggaataa actaatccgt acgctaacta atggacggat    2820
tatcctaagg gtcaccggct caccgttgga tataacactt agggtatggg agagctgata    2880
gaaatattgt actgtacaat ccaaagtaca gatagcacac gaagtatggt agttggtccc    2940
gcccagtccg gaccaacaat agaacaatac acgcacgagc agccgtccac tacgcagcag    3000
tgtgcgttcc tgaggacctg caggaagagg gggggggggg ggttgccaag acgcccgggg    3060
ttcaaagaaa gtcccgggcc gccgatgaga tgagacggac gccggcccaa ggagaggccg    3120
gtggtcgatc ctgcaaatgc cagcaaaaaa atccatacca taatccagtc aactttcgtc    3180
acactcctgt gaaacgagct ggagggactg ctggaaaggt tttgcaggtt aatcactgta    3240
tgtggagcat gccgtaccta ccatgcttcg ttagatagag ttccagttga acatacaaag    3300
ttctgccccg                                                          3310
```

<210> SEQ ID NO 6
<211> LENGTH: 389
<212> TYPE: PRT
<213> ORGANISM: Myceliophthora thermophila

<400> SEQUENCE: 6

Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Glu Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Val Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
                245                 250                 255

Trp Ser Trp Asn Thr Thr Asn Thr Asn Met Ala Ala Leu Thr Asp Pro
            260                 265                 270

Gln Asn Lys Ile Val Tyr Glu Met His Gln Tyr Leu Asp Ser Asp Ser
        275                 280                 285

Ser Gly Thr His Ala Glu Cys Val Ser Ser Asn Ile Gly Ala Gln Arg
    290                 295                 300

Val Val Gly Ala Thr Gln Trp Leu Arg Ala Asn Gly Lys Leu Gly Val
305                 310                 315                 320

Leu Gly Glu Phe Ala Gly Gly Ala Asn Ala Val Cys Gln Gln Ala Val
                325                 330                 335

Thr Gly Leu Leu Asp His Leu Gln Asp Asn Ser Asp Val Trp Leu Gly
            340                 345                 350

Ala Leu Trp Trp Ala Ala Gly Pro Trp Trp Gly Asp Tyr Met Tyr Ser
        355                 360                 365

Phe Glu Pro Pro Ser Gly Thr Gly Tyr Val Asn Tyr Asn Ser Ile Leu
    370                 375                 380

Lys Lys Tyr Leu Pro
385

<210> SEQ ID NO 7
<211> LENGTH: 31
<212> TYPE: DNA
<213> ORGANISM: Artificial Sequence
<220> FEATURE:
<223> OTHER INFORMATION: Direct primer - Oligonucleotide 1

<400> SEQUENCE: 7
accgagctcg tagcactcgc tgtgtatcct c                                31

<210> SEQ ID NO 8
<211> LENGTH: 34
<212> TYPE: DNA
<213> ORGANISM: Artificial Sequence
<220> FEATURE:
<223> OTHER INFORMATION: Reverse primer - Oligonucleotide 2

<400> SEQUENCE: 8
cctggatccc ttatacccag gacattcaca gttc                             34

<210> SEQ ID NO 9
<211> LENGTH: 32
<212> TYPE: DNA
<213> ORGANISM: Artificial Sequence
<220> FEATURE:
<223> OTHER INFORMATION: Direct primer - Oligonucleotide 3

<400> SEQUENCE: 9
accgaattca tcaaatggat aggtcggtaa tg                               32

<210> SEQ ID NO 10
<211> LENGTH: 31
<212> TYPE: DNA
<213> ORGANISM: Artificial Sequence
<220> FEATURE:
<223> OTHER INFORMATION: Reverse primer - Oligonucleotide 4

<400> SEQUENCE: 10
cacctcgagc aaggaagtcg agtacgagtc c                                31

<210> SEQ ID NO 11
<211> LENGTH: 21
<212> TYPE: DNA
<213> ORGANISM: Artificial Sequence
<220> FEATURE:
<223> OTHER INFORMATION: Direct primer - Oligonucleotide 5

<400> SEQUENCE: 11
ggctcgagat ctacaagact g                                           21

<210> SEQ ID NO 12
<211> LENGTH: 20
<212> TYPE: DNA
<213> ORGANISM: Artificial Sequence
<220> FEATURE:
<223> OTHER INFORMATION: Reverse primer - oligonucleotide 6

<400> SEQUENCE: 12
gtagttggac acgttggtga                                             20